(12) United States Patent
Bremer et al.

(10) Patent No.: US 8,212,058 B2
(45) Date of Patent: Jul. 3, 2012

(54) FLUORESCENT PHOTOPROBE FOR THE IMAGING OF ENDOTHELIN RECEPTORS

(75) Inventors: Christoph Bremer, Münster (DE); Carsten Höltke, Münster (DE); Klaus Kopka, Münster (DE); Michael Schäfers, Münster (DE)

(73) Assignee: Universitatskilinikum Munster, Munster (DE)

( * ) Notice: Subject to any disclaimer, the term of this patent is extended or adjusted under 35 U.S.C. 154(b) by 407 days.

(21) Appl. No.: 12/065,982

(22) PCT Filed: Sep. 6, 2006

(86) PCT No.: PCT/EP2006/008701
§ 371 (c)(1),
(2), (4) Date: Oct. 24, 2008

(87) PCT Pub. No.: WO2007/028599
PCT Pub. Date: Mar. 15, 2007

(65) Prior Publication Data
US 2009/0169483 A1    Jul. 2, 2009

(30) Foreign Application Priority Data
Sep. 6, 2005    (EP) .................................. 05019326

(51) Int. Cl.
*C07D 305/12*    (2006.01)
(52) U.S. Cl. ...................................... 549/320
(58) Field of Classification Search ............ 549/320
See application file for complete search history.

(56) References Cited

FOREIGN PATENT DOCUMENTS
WO    WO9818497    5/1998

OTHER PUBLICATIONS

Aleksic, et al. (2001) In Vivo Labeling of Endothelin Receptors with [$^{11}$C]L-753,037: Studies in Mice and a Dog. Journal of Nuclear Medicine, 42: 1274-1280.

(Continued)

*Primary Examiner* — Taylor Victor Oh
(74) *Attorney, Agent, or Firm* — Kagan Binder, PLLC

(57) ABSTRACT

The present invention relates to a endothelin receptor antagonist conjugate of the formula (I) wherein $R_2$ is an alkoxy group and one of $R_1$ and $R_3$ represents an alkoxy group and the other represents a group of the formula: $(OCH_2CH_2)_n$—NH—X, wherein n is an integer of 1 to 100 and X represents a fluorescent dye and tautomers thereof. Furthermore, the present invention relates to a diagnostic composition comprising the compounds of the invention. The present invention also relates to the use of the compounds of the invention for the preparation of a diagnostic composition for the diagnosis of cancer, the evaluation of cancer biology and/or monitoring of anticancer therapy. In a further aspect, the present invention relates to kits comprising the compounds of the invention.

7 Claims, 16 Drawing Sheets

Figure 1:
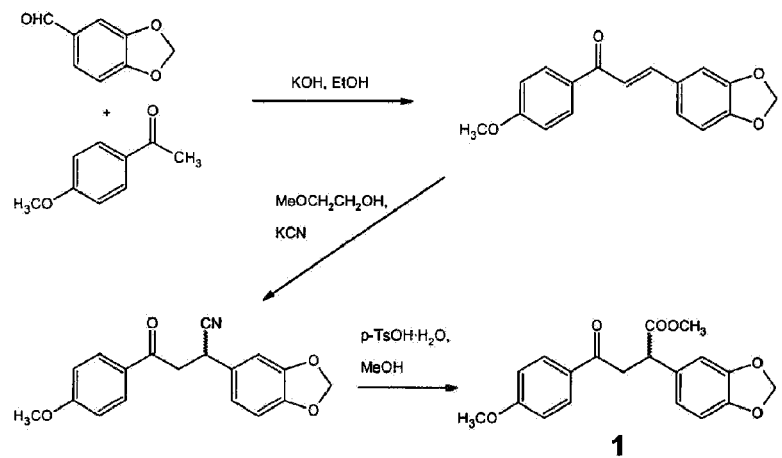
Figure 1:
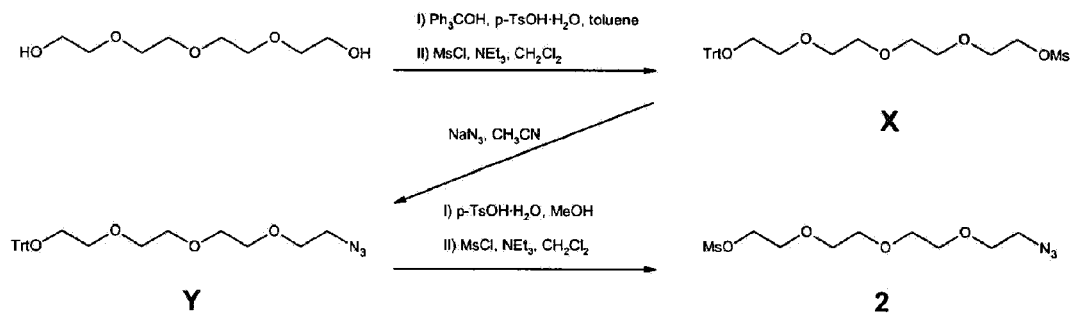

Synthesis of ketoester 1.

Synthesis of PEG-spacer 2.

OTHER PUBLICATIONS

Johnstrom, et al. (2000) Syntheses of the First Endothelin-A- and -B-Selective Radioligands for Positron Emission Tomography. Journal of Cardiovascular Technology, 36: 558-560.

Maguire, et al. (1997) Affinity and Selectivity of PD156707, A Novel Nonpeptide Endothelin Antagonist, for Human $ET_A$ and $ET_B$ Receptor. Journal of Pharmacology and Experimental Therapeutics, 280: 1102-1108.

Okamoto, et al. (2000) Cholesterol Oxidation Switches the Internalization Pathway of Endothelin Receptor Type A from Caveolae to Clathrin-coated Pits in Chinese Hamster Ovary Cells. Journal of Biological Chemistry, 275: 6439-6446.

Patt, et al. (1997) Structure-Activity Relationships in a Series of Orally Active γ-Hydroxy Butenolide Endothelin Antagonists. Journal of Medicinal Chemistry, 40: 1063-1074.

Ravert, et al. (2000) Radiosynthesis of a Potent Endothelin Receptor Antagonist: [$^{11}$C]L-753,037. Journal of Labelled Compounds and Radiopharmaceuticals, 43: 1205-1210.

Zemanova, et al. (2004) Endothelin Receptor in Virus-Like Particles: Ligand Binding Observed by Fluorescence Fluctuation Spectroscopy. Biochemistry 43: 9021-9028.

PCT International Search Report for International Application No. PCT/EP2006/008701 mailed on Sep. 10, 2007.

Oregon Green® 488 carboxylic acid, succinimidyl ester *6-isomer*, Material Safety Data Sheet, Molecular Probes, Inc., Aug. 3, 2004.

5-(and-6)-carboxy-X-rhodamine, succinimidyl ester (5(6)-ROX, SE) *mixed isomers*, Material Safety Data Sheet, Molecular Probes, Inc., Aug. 3, 2004.

QSY® 9 carboxylic acid, succinimidyl ester, Material Safety Data Sheet, Molecular Probes, Inc., Aug. 3, 2004.

6-((7-amino-4-methylcoumarin-3-acetyl)amino)hexanoic acid, succinimidyl ester (AMCA-X, SE), Material Safety Data Sheet, Molecular Probes, Inc., Aug. 3, 2004.

6-((5-dimethylaminonaphthalene-1-sulfonyl)amino)hexanoic acid, succinimidyl ester (dansyl-X, SE), Material Safety Data Sheet, Molecular Probes, Inc., Aug. 3, 2004.

7-dimethylaminocoumarin-4-acetic acid, succinimidyl ester (DMACA, SE), Material Safety Data Sheet, Molecular Probes, Inc., Aug. 3, 2004.

Dapoxyl® carboxylic acid, succinimidyl ester, Material Safety Data Sheet, Molecular Probes, Inc., Aug. 3, 2004.

Synthesis of ketoester 1.

Synthesis of PEG-spacer 2.

Synthesis of model-compound 4 for competition binding assays.

Coupling of hydroxybenzaldehyde with the PEG-spacer, condensation with ketoester 2, reduction of the azide 6 to yield the amine 7, coupling with fluorochrome FITC – conjugate 8

CY 5.5 – conjugate 9

Cell binding assays with the human breast cancer cell line- MCF-7 (AK = blocked with antibodies)

native     blocked + ET$_A$-Cy 5.5    ET$_A$-Cy 5.5 native     blocked + ET$_A$-Cy 5.5    ET$_A$-Cy 5.5 a)

b)

c)

FLUORESCENT PHOTOPROBE FOR THE IMAGING OF ENDOTHELIN RECEPTORS

This application is a 35 U.S.C. §371 National Stage application of International Application No. PCT/EP2006/008701, filed Sep. 6, 2006, designating the United States, which claims priority to EP Patent Application No. 05019326.7 filed Sep. 6, 2005, both of which are hereby incorporated in their entirety by reference.

The present invention relates to a endothelin receptor antagonist conjugate of the formula (I)

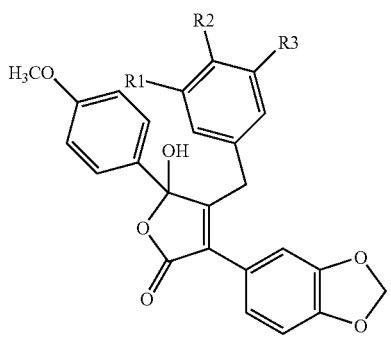

wherein $R_2$ is an alkoxy group and one of $R_1$ and $R_3$ represents an alkoxy group and the other represents a group of the formula: $(OCH_2CH_2)_n$—NH—X, wherein n is an integer of 1 to 100 and X represents a fluorescent dye, and tautomers thereof. Furthermore, the present invention relates to a diagnostic composition comprising the compounds of the invention. The present invention also relates to the use of the compounds of the invention for the preparation of a diagnostic composition for the diagnosis of cancer, the evaluation of cancer biology and/or monitoring of anti-cancer therapy. In a further aspect, the present invention relates to kits comprising the compounds of the invention.

A variety of documents is cited throughout this specification. The disclosure content of said documents (including any manufacturer's specifications, instructions etc.) is herewith incorporated by reference; however, there is no admission that any document cited is indeed prior art as to the present invention.

Since endothelin (ET) was first described by Hickey et al.[1] and subsequently isolated by Yanagisawa et al.[2] as a 21-amino acid peptide with vasoactive potential, the role of the endothelins in several diseases, including atherosclerosis, congestive heart failure and pulmonary hypertension, has been increasingly investigated.[3-7] In addition, the role of endothelin as a progression factor in many human tumor cell lines has recently been discussed. Three isoforms of endothelin exist (ET-1, ET-2 and ET-3), exerting their effects via two different G-protein coupled receptors ($ET_A$, $ET_B$). $ET_A$ receptors are primarily located on vascular smooth muscle cells and are responsible for vasoconstriction and cell proliferation, whereas $ET_B$ receptors are located on smooth muscle cells and vascular endothelial cells, cause vasodilation by the release of nitric oxide and prostacyclin and are responsible for the clearance of ET-1 from plasma.[8-13] The affinity of ET-1 and ET-2 to the $ET_A$ receptor is about a hundred fold higher than the affinity of ET-3. The affinity to the $ET_B$ receptor, however, is equal for all three isoforms.[14-17] All native endothelins, therefore, represent nonselective ET receptor substrates.

Plasma levels of ET-1 are elevated in many cardiovascular diseases. In this connection it has been shown that in mouse models of human atherosclerosis (apoE$^{-/-}$) $ET_A$ receptor density is upregulated in atherosclerotic plaques.[18,19] Consequently, ET receptor antagonists are used in the treatment of these diseases, and a number of different peptidyl and non-peptidyl ligands, both selective and nonselective, have been developed in attempts to improve efficacy.[20-27] In addition to its role in cardiovascular diseases, ET-1 is also an important factor in the pathophysiology of certain human cancers. Recent data suggest that especially ET-1 is relevant in the progression of a variety of tumor types such as prostatic, breast and ovarian carcinoma,[28] Karposi's sarcoma, melanoma and lung malignancies. In these cases endothelins play a role as paracrine as well as autocrine factors, promoting tumor growth by inducing cell proliferation and angiogenesis and inhibiting apoptosis.[29,30]

In this context, a method for the visualization of ET receptor density in affected tissue would be invaluable for clinical diagnosis and the evaluation of therapy. The radiolabelling of ET receptor agonists and antagonists has been reported,[34-42] but none of the approaches have been utilised for the in vivo imaging of ET receptors in humans.

Thus, the technical problem underlying the present invention was to provide means and methods for the non-invasive detection of molecular targets (i.e. cells or tissues expressing endothelin receptors) that promote or are associated with tumor progression.

The solution to said technical problem is achieved by providing the embodiments characterized in the claims.

The ability to non-invasively detect molecular targets that promote or are associated with tumor progression greatly enhances the ability for (a) early diagnosis of cancer, (b) the evaluation of cancer biology (i.e. 'grading') leading to specific treatment protocols and finally (c) monitoring of molecular targeted anti-cancer therapy. The compounds of the present invention represent biocompatible, targeted fluorochromes which exhibit a high affinity for the endothelin A receptor, a target which is strongly involved in carcinogenesis. The molecule was designed to exhibit a low molecular weight so that the tracer can be rapidly eliminated from the circulation.

Thus, in a first aspect, the present invention relates to an endothelin receptor antagonist conjugate of formula (I)

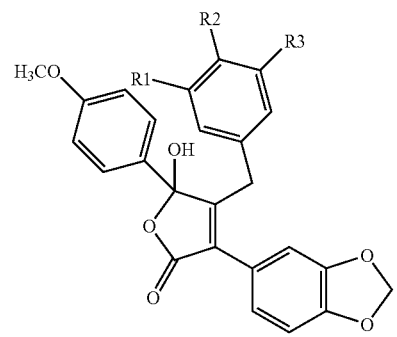

wherein
  $R_2$ is an alkoxy group and one of $R_1$ and $R_3$ represents an alkoxy group and the other represents a group of the formula:
    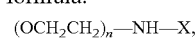
    $(OCH_2CH_2)_n$—NH—X,
  wherein n is an integer of 1 to 100
  and X represents a fluorescent dye and tautomers thereof.

Large molecules (e.g. wherein n=25-100) will exhibit a 'Blood pool' effect which is considered to be advantageous for specific body compartments or tumor pathology, respectively. Small (i.e.: where n is an integer of about 2 to 10, preferably 4) will be excreted more rapidly from the system which is advantageous for in vivo use.

The term "alkoxy" as used herein is meant to include linear or branched $C_1$-$C_{12}$, preferably $C_1$-$C_6$ alkoxy; e.g. methoxy, ethoxy, iso-proproxy, n-proproxy, iso-butoxy, n-butoxy, sec.-butoxy, tert.-butoxy, n-pentoxy, iso-pentoxy, sec.-pentoxy, tert.-pentoxy, neo-pentoxy, n-hexoxy, 1-methylpentoxy, 2-methylpentoxy, 3-methylpentoxy, 4-methylpentoxy, 1-ethylbutoxy, 2-ethylbutoxy, 1,1-dimethylbutoxy, 2,2,-dimethylbutoxy or 3,3-dimethylbutoxy. Methoxy is preferred.

In a preferred embodiment $R_1$ and $R_2$ are $OCH_3$.

The present invention particularly prefers compounds wherein n=4.

It must be noted that as used herein, the singular forms "a", "an", and "the", include plural references unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

In another aspect of the compounds of the present invention the absorption maximum of the fluorescent dye is from about 600 nm to 850 nm.

In a preferred embodiment of the compounds of the invention the fluorescent dye is selected from Cy 5, Cy 5.5, Cy 7, C 3, Cy 3.5, fluorescein (FITC), heptamethylene thiocyanine, ROX, TAMRA, CAL Red, Red 640, FAM, TET, HEX, Oregon Green, TRITC, APC, DY-751, ATTO 740, ATTO 725 and ATTO 700. Particularly preferred are Cy 5, Cy 5.5 and Cy 7.

The fluorescent dyes as described herein are well-known to the skilled person and furthermore commercially available e.g. at Amersham Biosciences Europe GmbH, Freiburg, Germany; Dyomics GmbH, Jena, Germany; MoBiTec GmbH, Gottingen, Germany; Invitrogen GmbH, Karlsruhe, Germany.

In a most preferred embodiment the compound is selected from

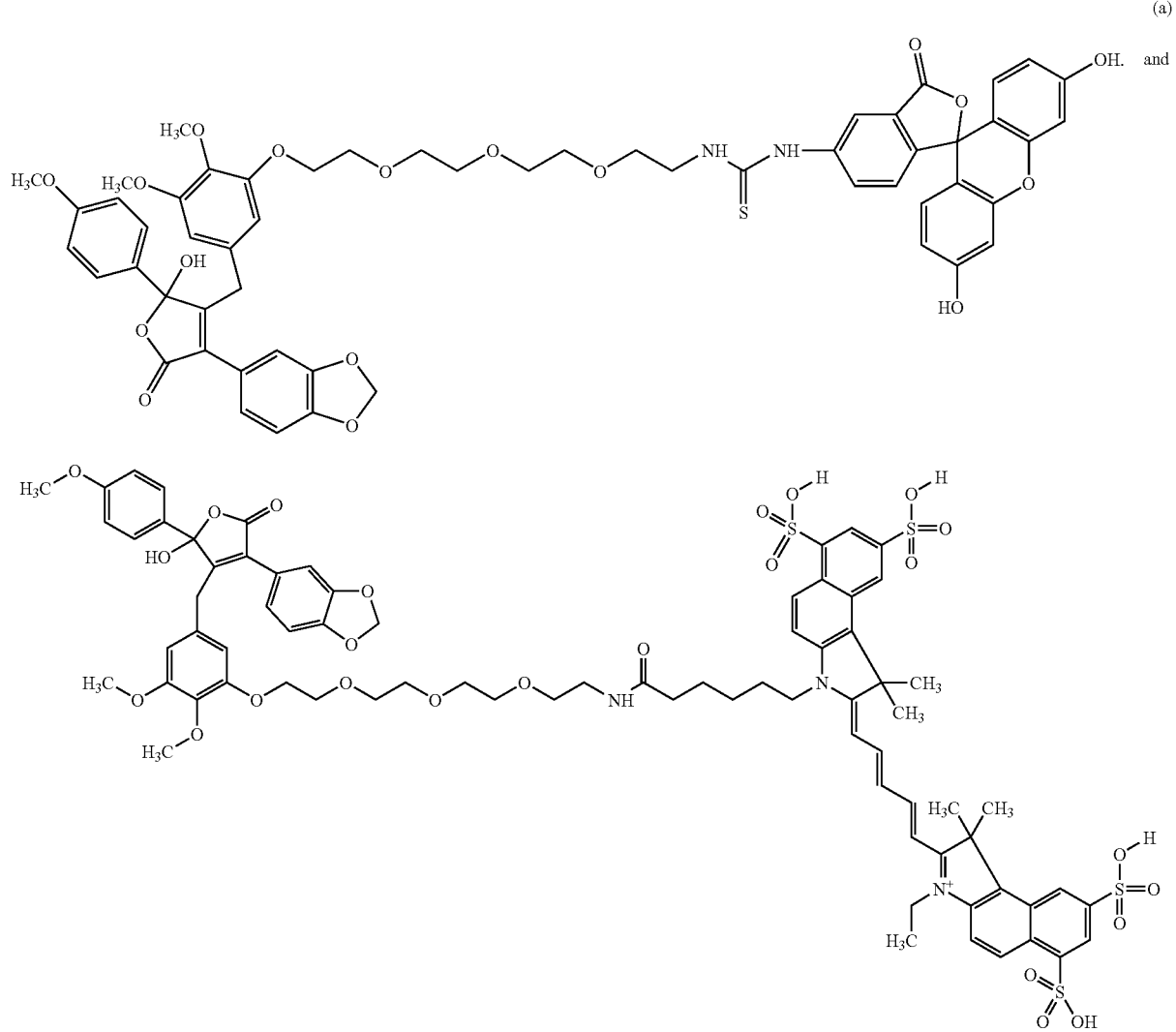

and tautomers thereof.

PD 156707 3 (3-Benzo[1,3]dioxol-5-yl-5-hydroxy-5-(4-methoxyphenyl)-4-(3,4,5-tri-methoxybenzyl)-5H-furan-2-one, FIG. 1) and related butenolide derivatives are potent ET receptor antagonists with high affinity and $ET_A$ selectivity.[43-48] In this study we describe the synthesis of a modified ligand with a PEG-spacer group and an amino functionality. The conjugation of fluorescent dyes (FITC, Cy 5.5) to this ligand was accomplished by slightly modifying the common peptide-labelling procedures. A model compound with a shorter PEG spacer and a phthalimidoyl protecting group was synthesised and used in an affinity assay to evaluate the binding properties of such modified compounds towards ET receptors. PD 156707 3 was also synthesised and used as a competing inhibitor and for comparison of the affinity values. The Cy 5.5-modified ligand was used in in vitro binding assays with $ET_A$-positive MCF-7 human breast adenocarcinoma cells to test specific binding. Again, PD 156707 was used as a competing ligand.

Figure 5:
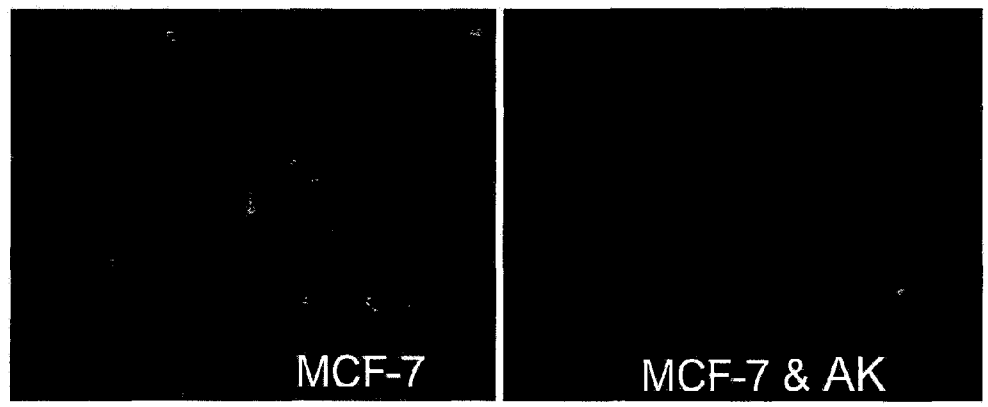

Novel fluorescent photoprobes for the imaging of endothelin (ET) receptors were developed. Based on the nonpeptide, highly affine and selective $ET_A$ receptor antagonist (3-Benzo[1,3]dioxol-5-yl-5-hydroxy-5-(4-methoxyphenyl)-4-(3,4,5-trimethoxybenzyl)-5H-furan-2-one (PD 156707), a modification of the lead structure with a PEG-spacer containing an amino moiety was performed. Labelling of this precursor with common peptide markers like FITC and Cy 5.5 was accomplished by slight modification of the known peptide-labelling procedure. The affinity of the Cy 5.5-labelled receptor antagonist towards ET-positive human breast carcinoma cell line MCF-7 was evaluated (FIG. 5). Fluorescence microscopy was used to show that MCF-7 cells can be imaged at very low doses (nM). Specific binding could be blocked by using the parent antagonist PD 156707 as a competing inhibitor. The results indicate that the modified photoprobe tightly binds to $ET_A$ receptors and thus qualifies as a potent candidate for the in vivo imaging of ET-overexpressing tissues.

In a further aspect, the present invention relates to a diagnostic composition comprising a compound of the invention as described herein and, optionally a diagnostic carrier.

Examples of "diagnostic carriers" are well known in the art and include phosphate buffered saline solutions, water, emulsions, such as oil/water emulsions, various types of wetting agents, sterile solutions etc. Compositions comprising such carriers can be formulated by well known conventional methods. These diagnostic compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

The diagnostic compositions of the invention are preferably employed for fluorescence mediated tomography (FMT). This imaging technique which is described for example in Ntziachristos V, Tung C-H, Bremer C, Weissleder R; Fluorescence-mediated tomography resolves protease activity in vivo; Nature Medicine 8 (7), 757-60 (2002), allows a three-dimensional, quantitative reconstruction of fluorochrome distibution in vivo. FMT can e.g. be applied to detect and quantify fluorophores accumulated in deep seated breast tissue. Moreover the targeted fluorochrome can be applied for different fluorescence reflectance imaging (FRI) techniques, which provide a surface weighted image of tissue fluorescence. FRI is a rapid technique that does not require image reconstruction. It can be miniturazied and thus incorporated into endoscospe, catheters or applied intra-operatively. (Ntziachristos N et al; Eur Radiol. 2003 January; 13(1):195-208. Epub 2002 Jul. 19. Review)

The present invention also relates to the use of a compound of the invention for the preparation of a diagnostic composition for the in vivo imaging of $ET_A$-receptor density, preferably in mammals, more preferably in humans.

The present invention also relates to the use of a compound of the invention for the preparation of a diagnostic composition for the diagnosis of cancer, the evaluation of cancer biology and/or monitoring of anti-cancer therapy. Specifically the detection of $ET_AR$ expressing breast cancers should be greatly facilitated. Moreover therapeutic concepts (e.g. the application of an $ET_AR$-inhibitor) can be based on the scanning results. The capabilities of the compounds of the invention thus facilitate patient selection for novel $ET_A$ receptor therapies. Finally the therapeutic efficacy (e.g. of an $ET_AR$-inhibitor) may be assessed non invasively.

In a preferred embodiment, said cancer is selected from breast cancer, ovarian cancer, cervical cancer, prostatate cancer, melanoma, sarcomas, lypmhomas, bone malignancies, renal cancer, lung cancer, colon cancer, Karposi's sarcoma and CNS tumors. See for example J. Nelson, A Bagnato, B. Battistini, P. Nisen: The endothelin axis: emering role in cancer; The endothelin axis: emerging role in cancer. Nat Rev Cancer. 2003 February; 3(2):110-6. Review.

It is particularly preferred that the compounds of the invention and uses as described herein are employed for fluorescent mediated tomography or fluorescence reflectance imaging methods (i.e.: surface weighted fluorescence reflectance imaging).

The term "fluorescent mediated tomography" has a well-recognized meaning and is further explained herein-above.

Altering the labelling and detection strategy towards optical imaging techniques like fluorescence reflectance imaging (FRI), fluorescence mediated tomography (FMT) or near infrared fluorescence (NIRF) imaging is an interesting alternative to the use of nuclear imaging techniques like single photon emission computed tomography (SPECT) or positron emission tomography (PET). While FRI is limited to superficial tissue structures, FMT offers the possibility of 3D quantitative imaging of photon absorption of tissue fluorescence in vivo. Combining these optical imaging techniques with targeted fluorescent probes offers excellent signal to noise ratios (SNRs) and thus very high sensitivity to detect molecular structures (such as cell receptors). Optical imaging techniques allow to delineate structures in the picomolar ($10^{-12}$) range, which is comparable to conventional nuclear imaging techniques and about 6 orders of magnitude more sensitive compared to MRI. Besides high SNRs imaging in the near infrared shows very efficient tissue penetration as the absorption by water and hemoglobin is relatively low ("diagnostic window").

In a further embodiment the present invention relates to a kit comprising a compound of the invention and optionally a solvent, diluent, buffer for stabilizing and/or storing the inventions compounds. Said kit may further comprise instruction manuals which guide the skilled person in carrying out the detection methods which are inter alia described herein (e.g. diagnosis of cancer, the evaluation of cancer biology and/or monitoring of anti-cancer therapy).

The dosage regimen utilising the inhibitors or screened compounds (inhibitors) of the present invention is selected in accordance with a variety of factors including type, species, age, weight, sex and medical condition of the patient; the severity of the condition to be treated; the route of administration; and the particular compound employed. It will be acknowledged that an ordinarily skilled physician or veterinarian can easily determine and prescribe the effective amount of the compound required to prevent, counter or arrest the progress of the condition.

THE FIGURES SHOW

FIG. 1 Synthesis of the butenolide compounds 4, 6 and 7

Figure 2:
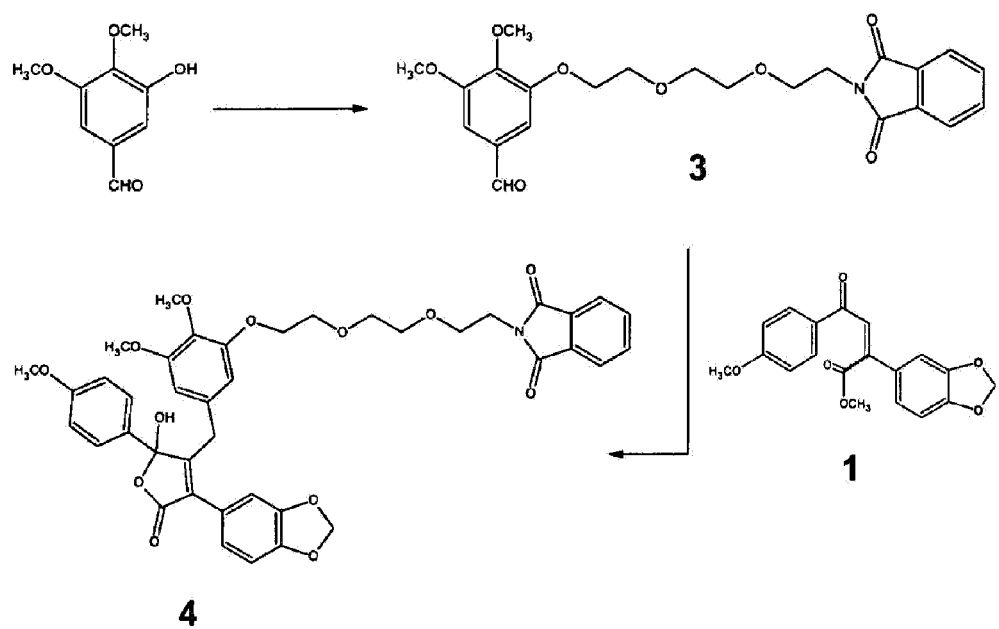

FIG. 2 Synthesis of model-compound 4 for competition binding assays.

Figure 3:
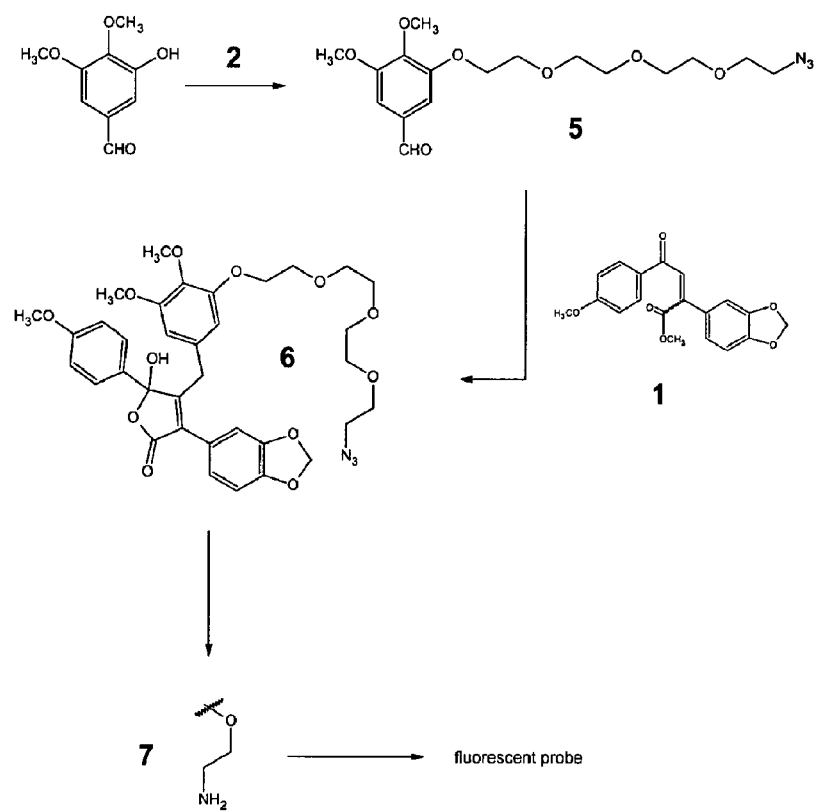
Figure 4:
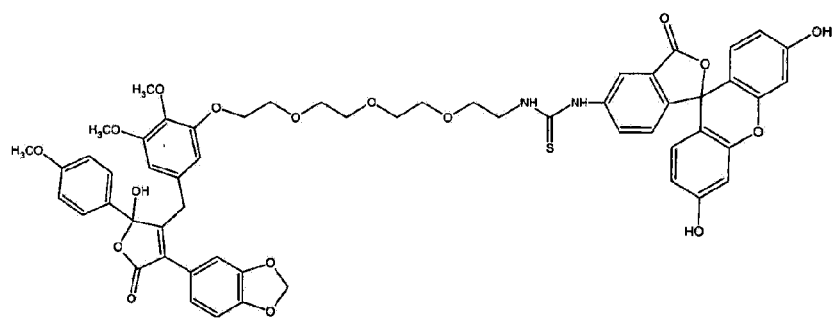
Figure 4:
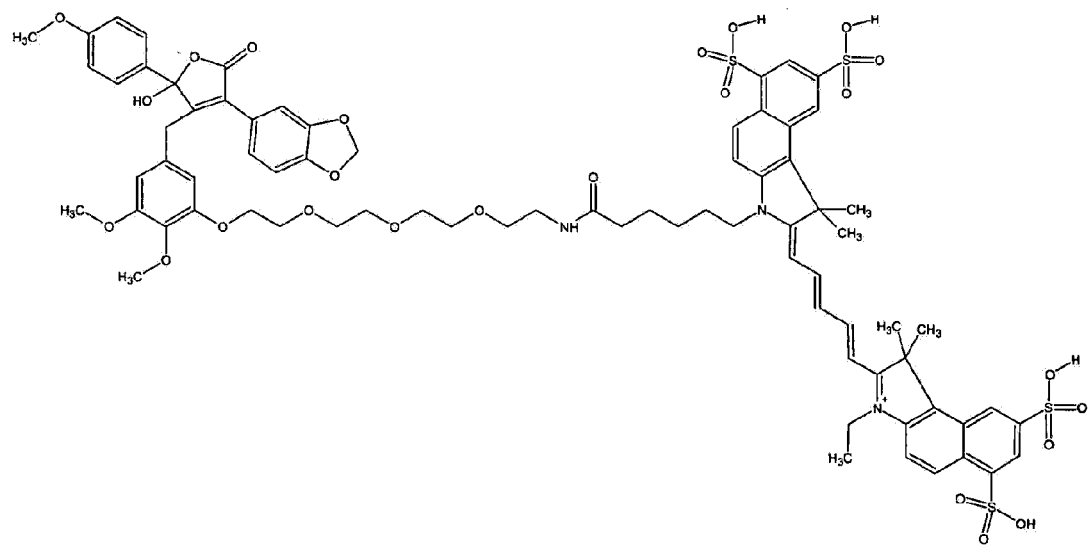

FIG. 3 Coupling of hydroxybenzaldehyde with the PEG-spacer, condensation with ketoester 2, reduction of the azide 6 to yield the amine 7, coupling with fluorochrome FIG. 4 FITC—conjugate 8 and CY 5.5—conjugate 9

Figure 6:
Figure 6:
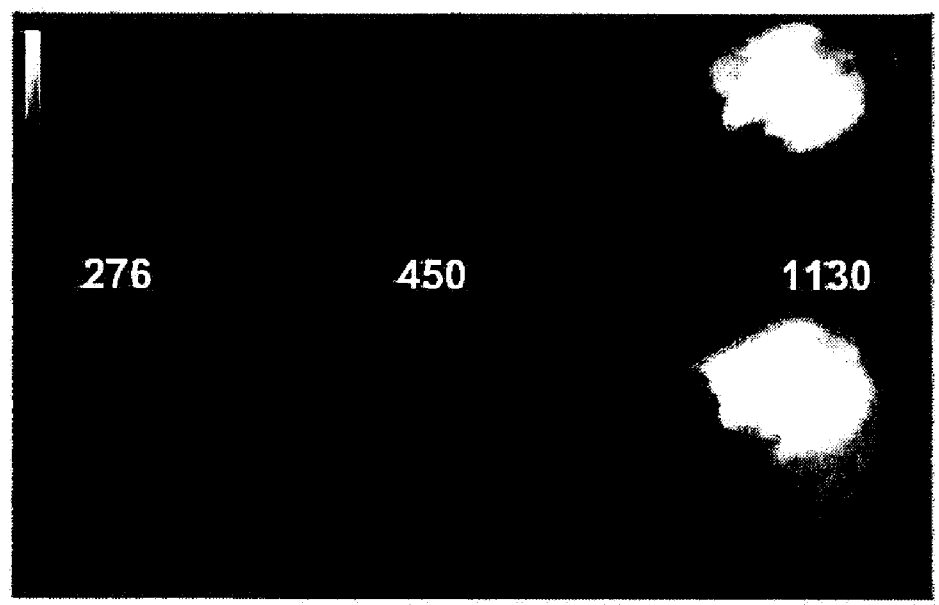

FIG. 5 Detection of $ET_AR$—expression on $ET_AR$-positive MCF-7 breast cancer cells using the targeted fluorochrome. Note the strong fluorescence signal (right) which could be significantly reduced by pre-dosing with an anti $ET_AR$ antibody FIG. 6: In vivo application of the targeted fluorophore for imaging of myocardial $ET_AR$—expression. Mice were injected with the targeted fluorophore with (middle) and without (right) pre-dosing with PD 156707. The left speciment is a saline injected control. Note that FRI obtained 10 min post injection shows a strong fluorophore accumulation in the myocardium (right upper row—color code data, lower row: raw data). This signal could be significantly reduced by pre-dosing with the parent antagonist PD 156707 which confirms the binding specificity of the probe in vivo.

Figure 7:
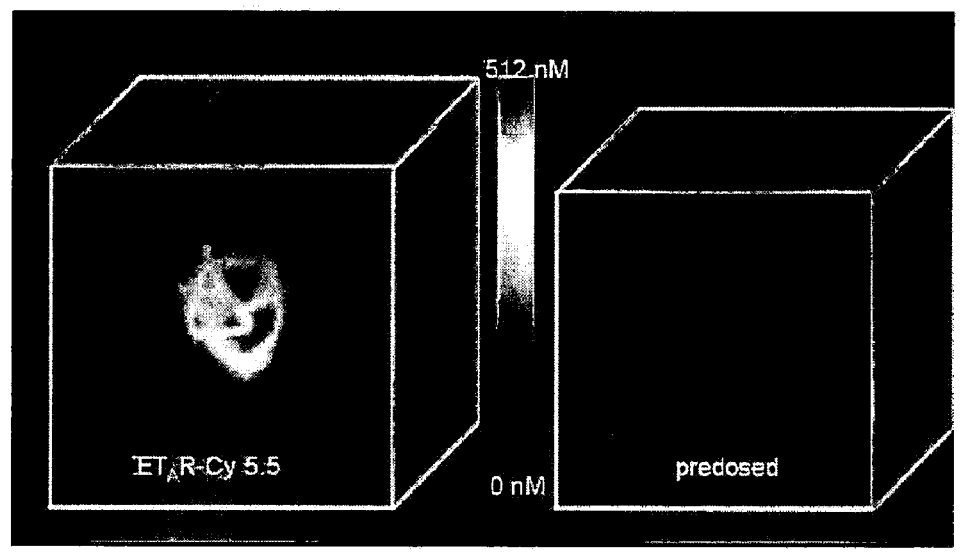
Figure 7:
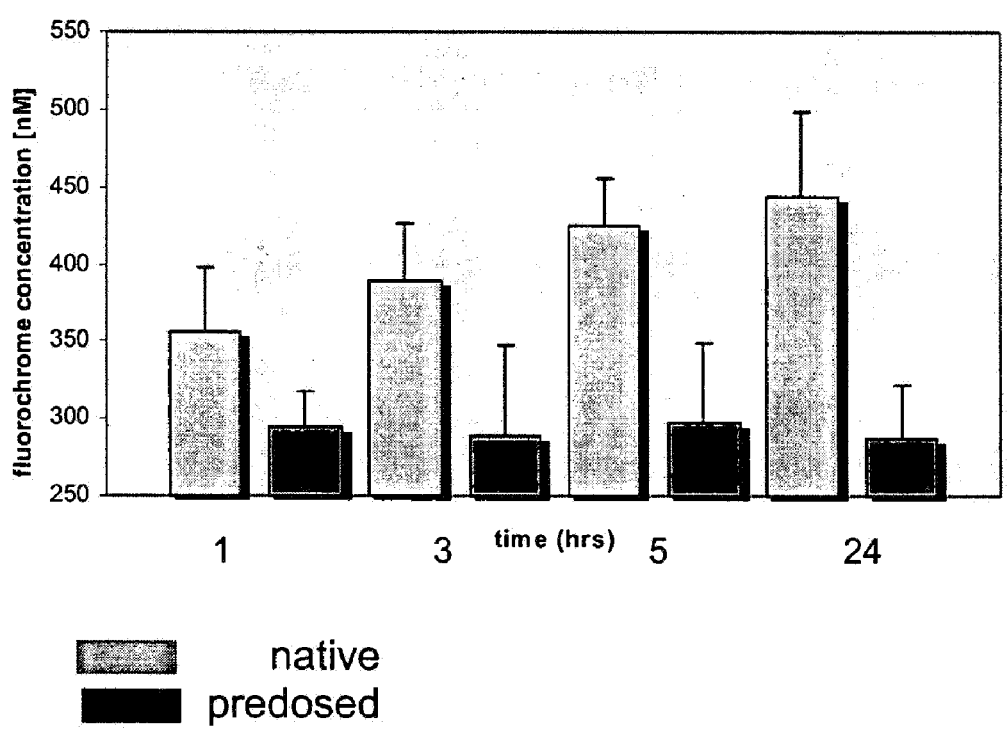

FIG. 7: 3D-FMTexamination of MDA-MB-435 murine xenograft models. Left: 24 hours after the application of 2 nmol $ET_AR$-Cy5.5 conjugate; Right: pre-dosing experiment, 10 minutes before applying the fluorescence marker, 100 nmol of unmodified antagonist (PD 156707) were injected; the time course representing the fluorochrome concentration after 1, 3, 5 and 24 hours is depicted as well.

Figure 8:
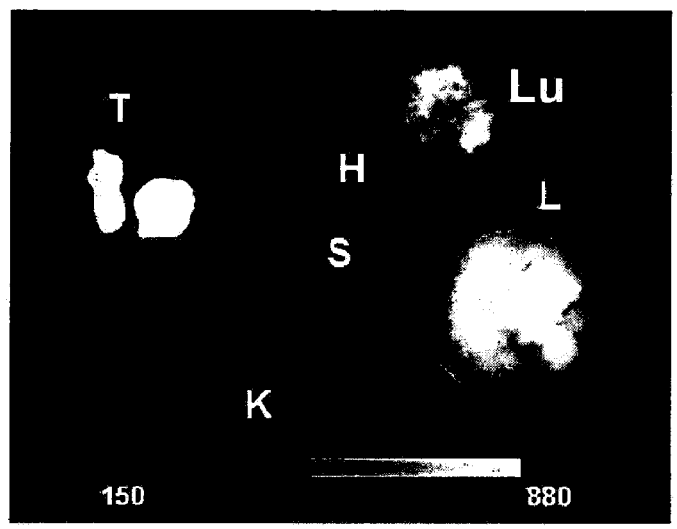
Figure 8:
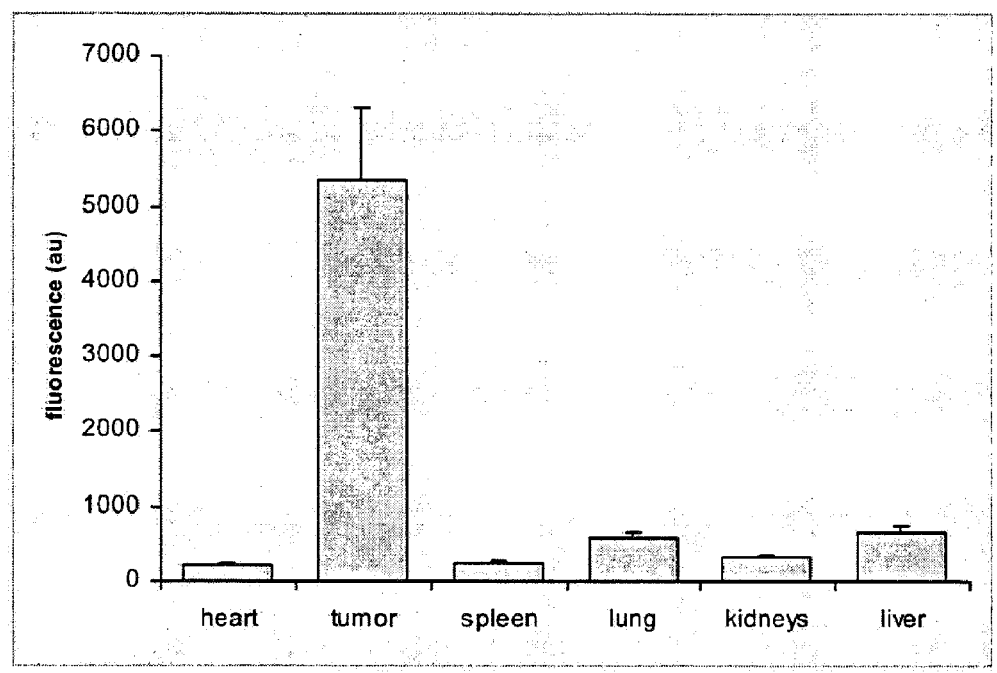
Figure 9:
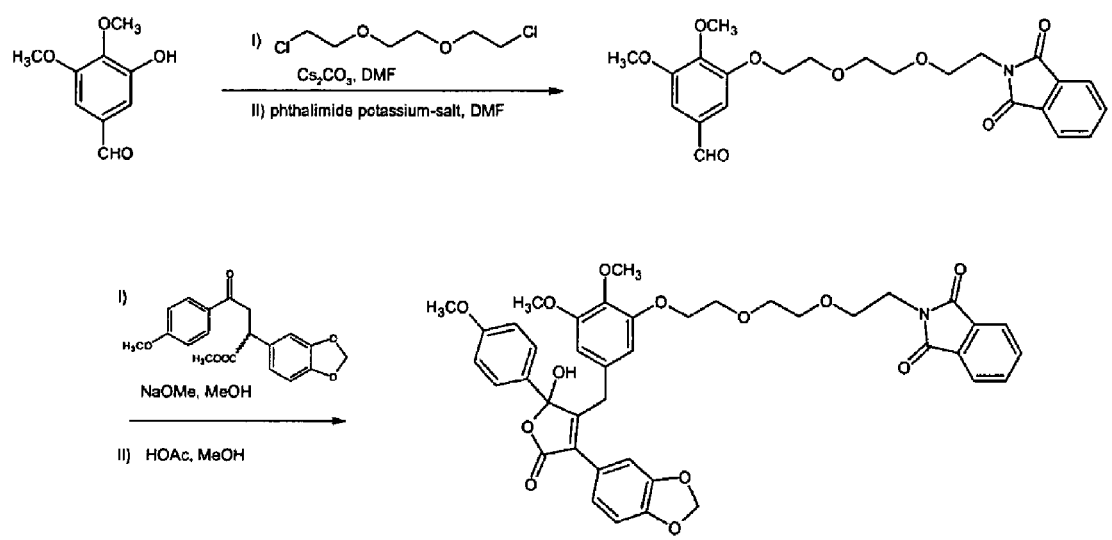

FIG. 8: 2D-FRI fluorescence imaging of explanted organs of a MDA-MB-435 murine xenograft model 24 hours after injecting 2 nmol $ET_AR$ Cy5.5 conjugate. b) statistical score(s) (n=5); abbreviations: T=tumor; H=heart, S=spleen, Lu=lung, L=liver, K=kidney FIG. 9: Preparation of model compound 4 of Example 14 (therein Scheme 1)

Figure 10:
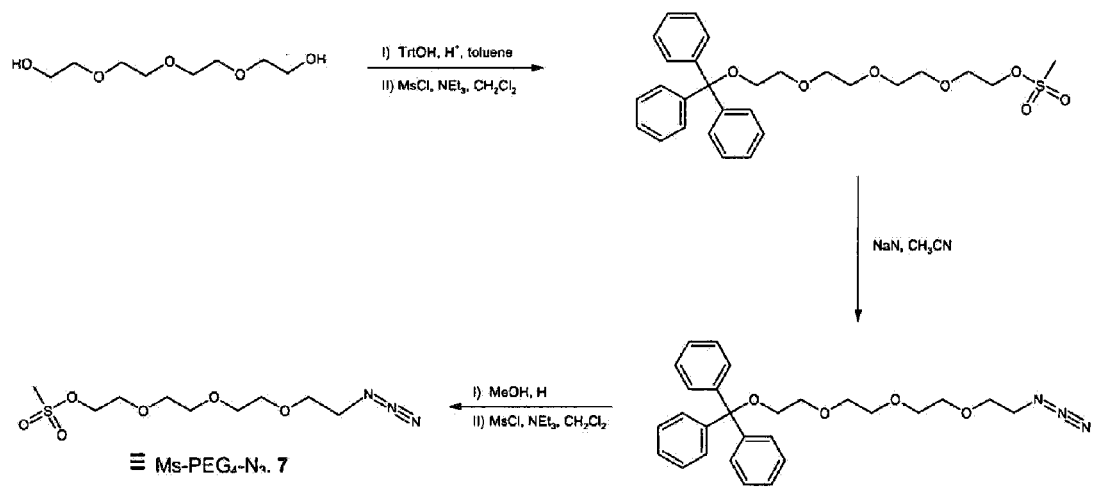

FIG. 10: Preparation of PEG-derivative MsO-PEG$_4$-N$_3$, 7 (adapted from Tahtaoui (38)) of Example 14 (therein Scheme 2)

Figure 11:
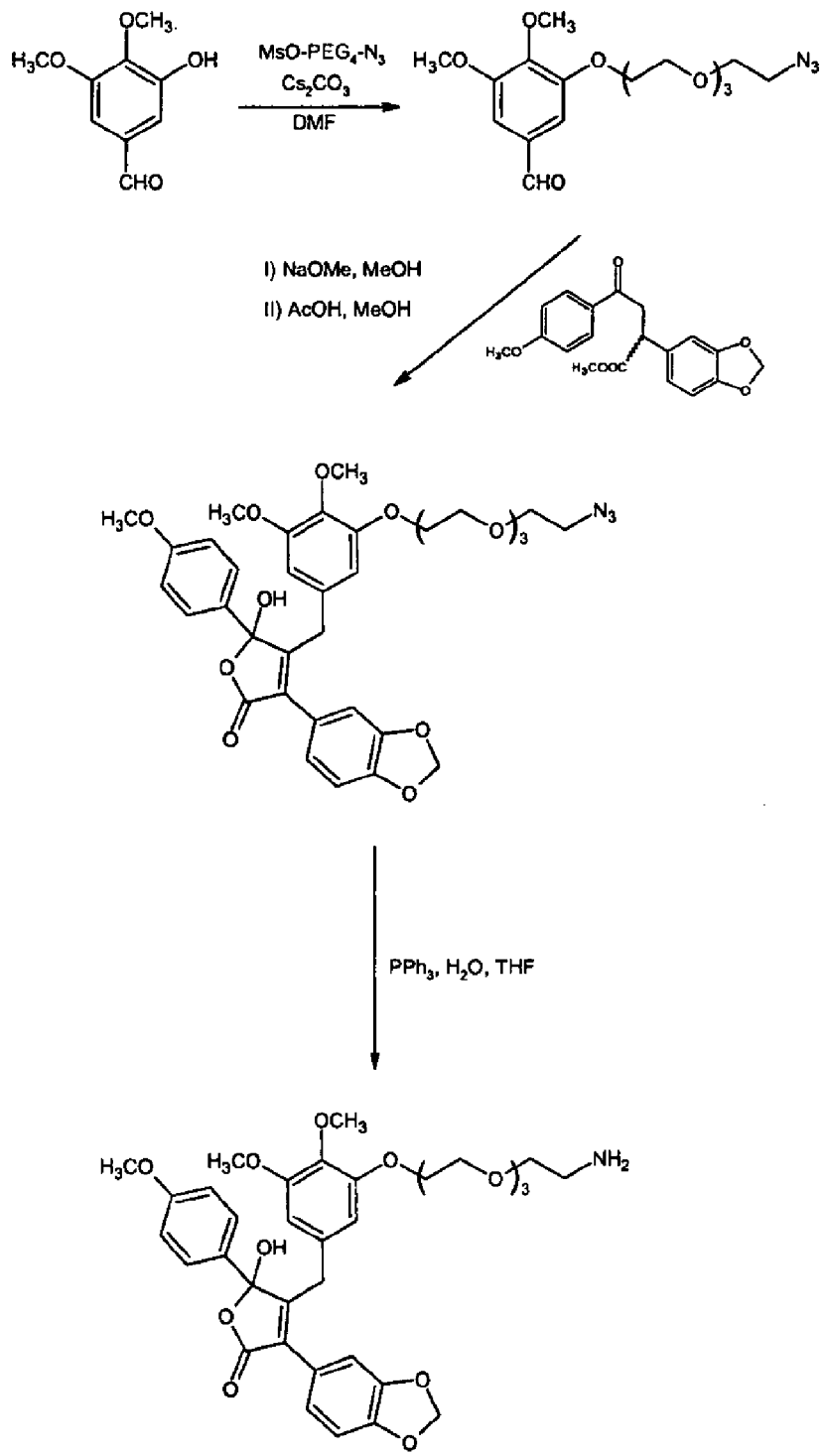

FIG. 11: Preparation of amino-functionalised target compound 10 of Example 14 by Staudinger reaction (therein Scheme 3)

Figure 12:
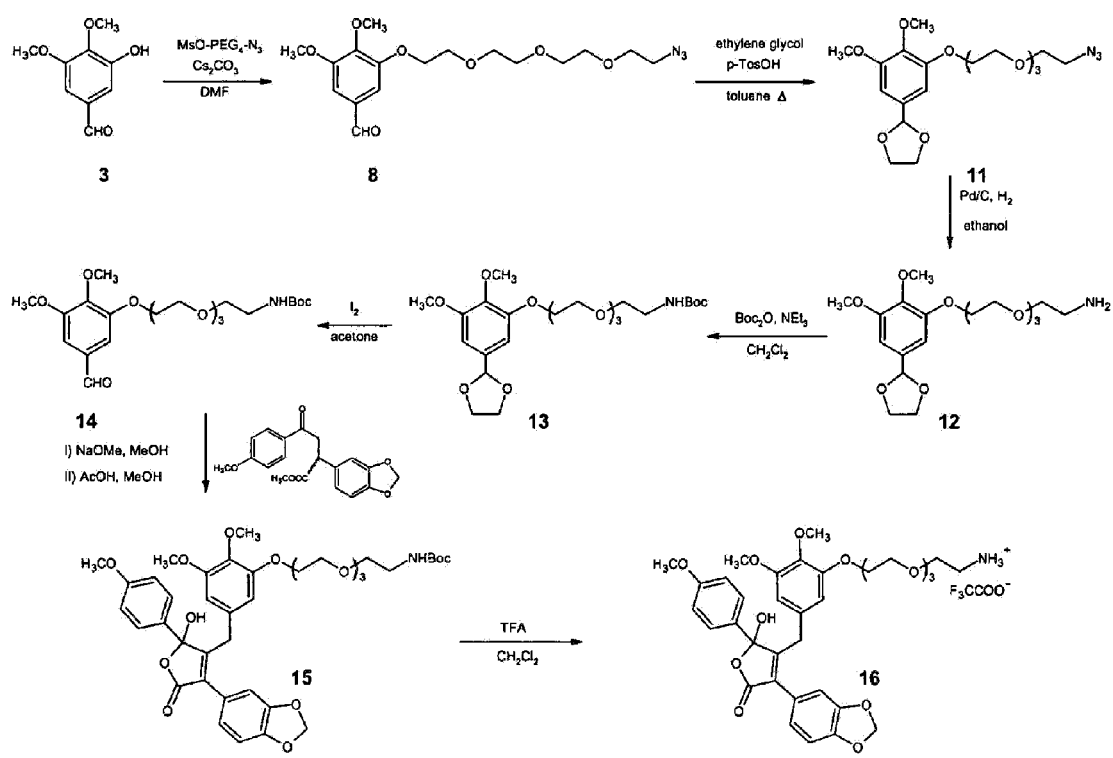

FIG. 12: Preparation of target compound 16 of Example 14 (therein Scheme 4)

Figure 13:
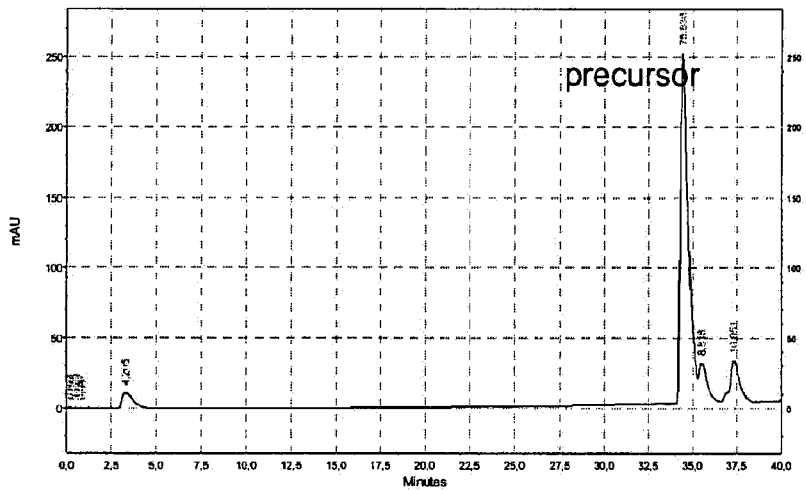
Figure 13:
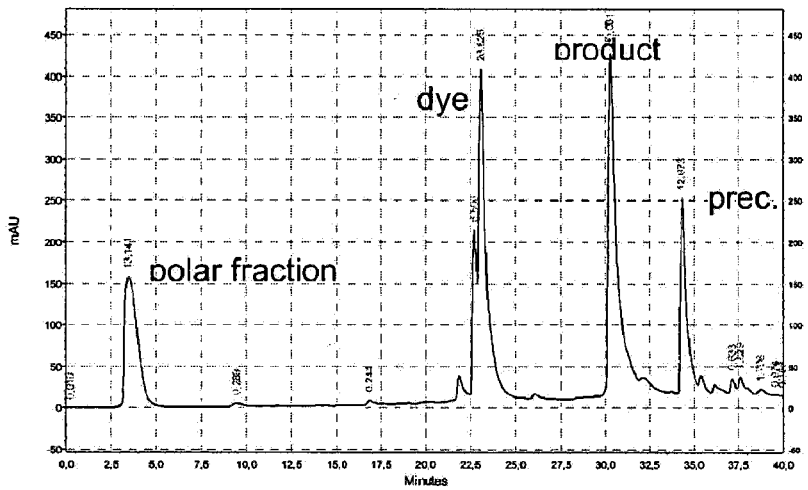
Figure 13:
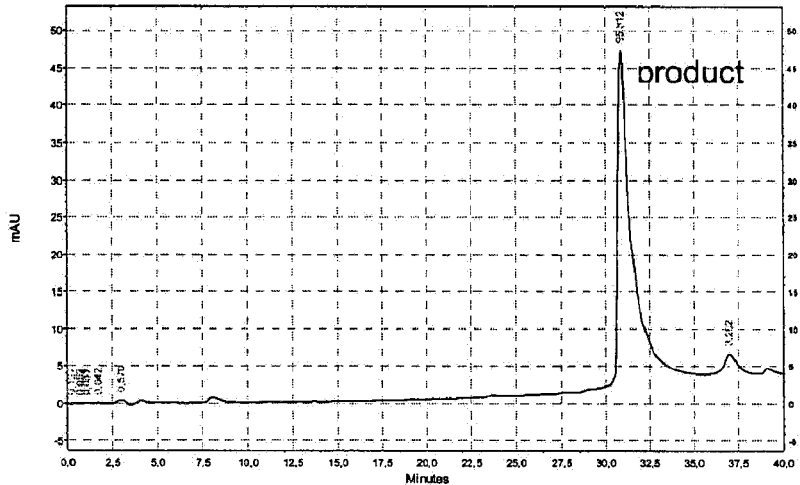

FIG. 13: HPLC-chromatograms of precursor 16 (a), a reaction mixture with Cy 5.5 NHS-Ester, bicarbonate buffer and DMSO (b) and the purified sample of conjugate 17 (c) as cited in Example 14 (therein FIG. 1)

Figure 14:
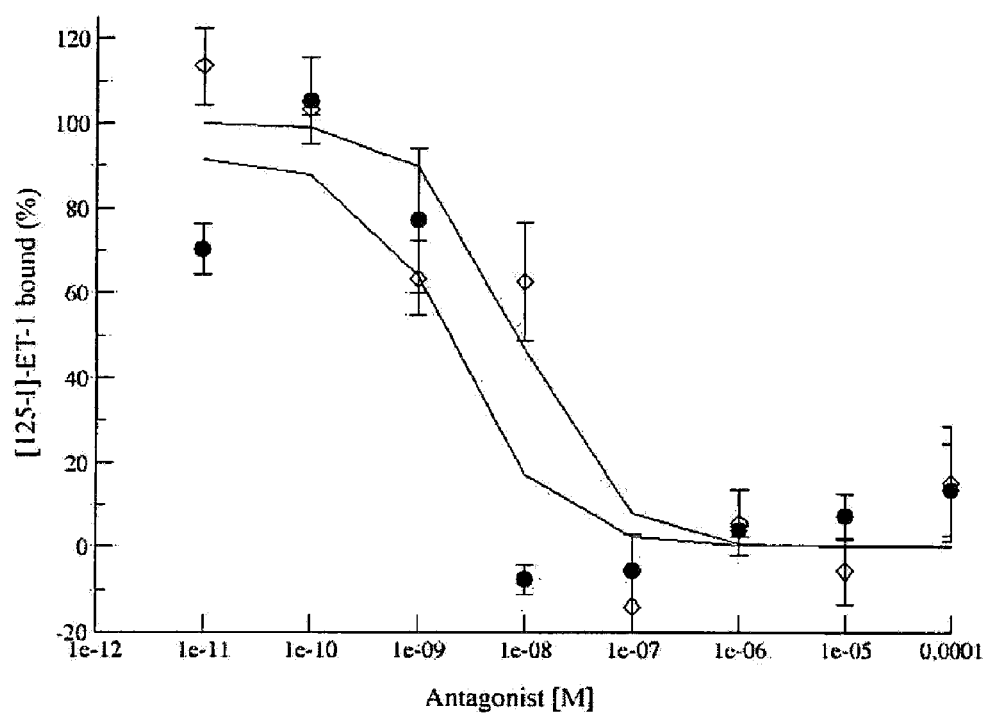

FIG. 14: Competition binding study with model compound 4 in comparison to lead structure PD 156707 (● PD 156707, $IC_{50}$=2.0 nM, ◇ Compd. 4, $IC_{50}$=9.0 nM) as cited in Example 14 (therein FIG. 2)

Figure 15:
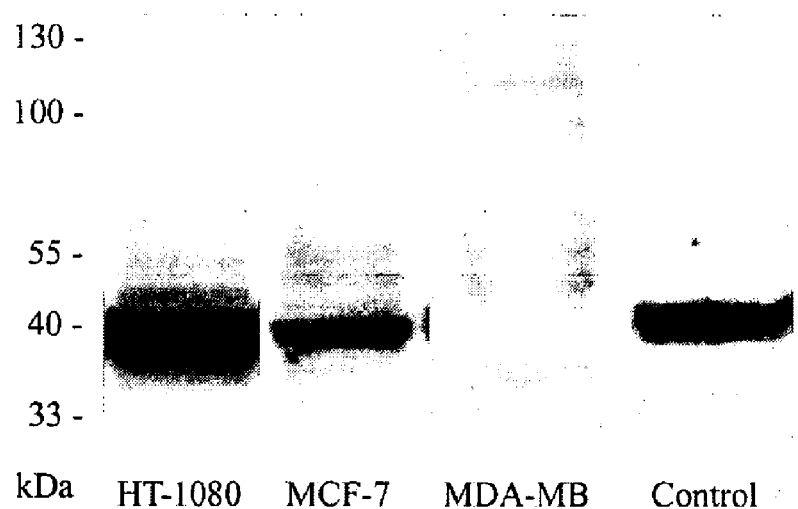

FIG. 15: Western blot analysis of the three used cell lines HT-1080, MCF-7 and MDA-MB435 (left to right) and human endothelial cell lysate as positive control (from left to right). HT-1080 fibrosarcoma cell show the highest expression level of $ET_AR$ while MCF-7 adenocarcinomas only moderately express the target structure and MDA-MB435 cells are devoid of the $ET_A$ receptor as cited in Example 14 (therein FIG. 3)

Figure 16:
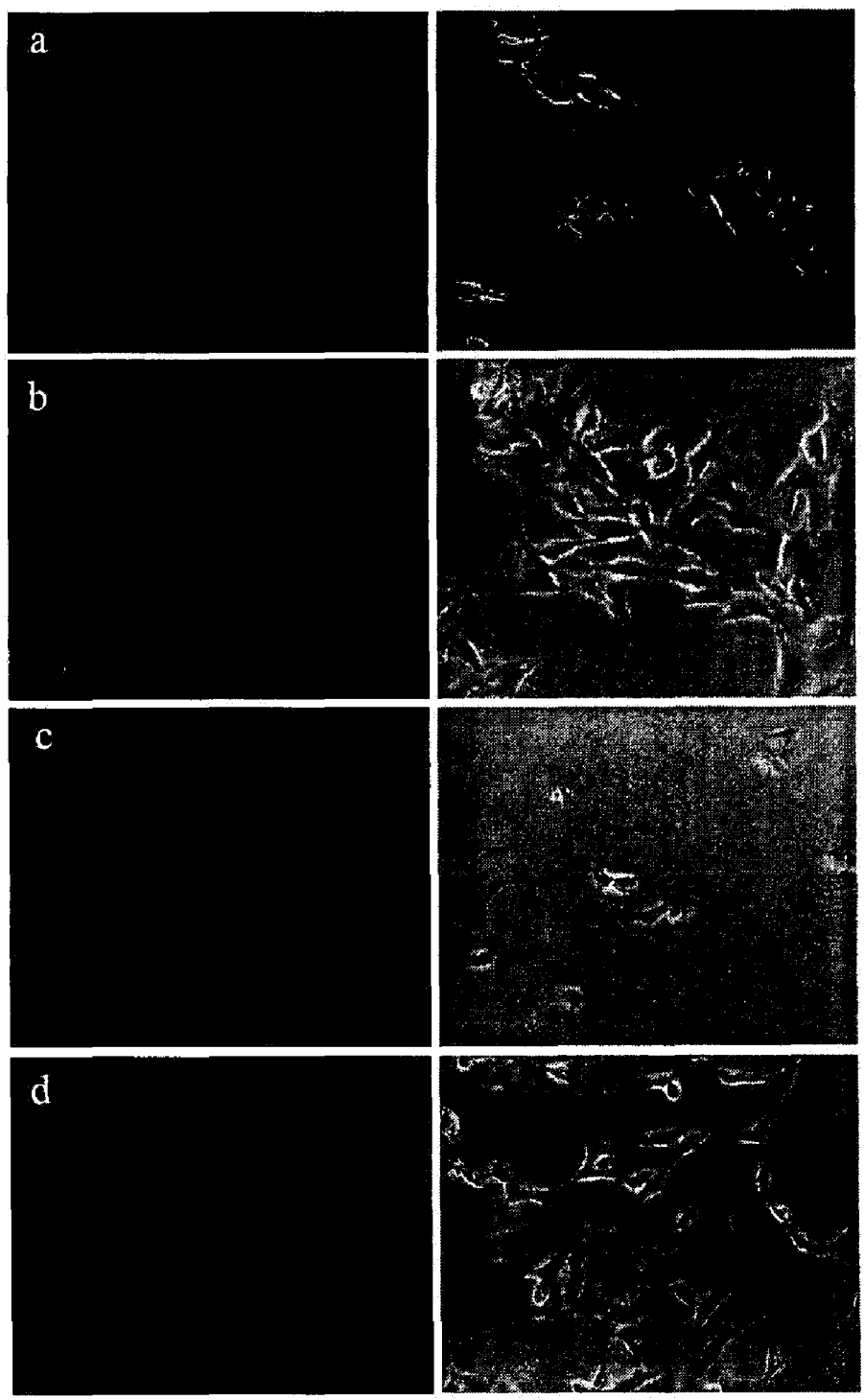

FIG. 16: Fluorescence microscopic (left) and phase contrast (right) images of HT-1080 (a), MCF-7 (c) and MDA-MB-435 (d) cells. All cells were incubated with conjugate 17 and subsequently washed with PBS. Note that HT-1080 cells reveal the highest cellular fluorescence (a) while MCF-7 cells show only moderate cellular fluorescence (c) and MDA-MB-435 do not bind the tracer (d). Moreover, predosing of HT-1080 cells with an $ET_AR$ specific antibody resulted in a significant reduction of cellular binding of the probe (b) confirming the binding specificity of Cy 5.5 conjugate 17 (40× objective magnification) as cited in Example 14 (therein FIG. 4)

EXAMPLES

The following examples illustrate the invention. These examples should not be construed as to limit the scope of this invention. The examples are included for purposes of illustration and the present invention is limited only by the claims.

Materials and Methods

All chemicals, reagents and solvents for the synthesis of the compounds were analytical grade and purchased from commercial sources. PD 156707 and 2-(benzo-[1,3]-dioxol-5-yl)-1-(4-benzyloxyphenyl)-4-oxobutyric acid methyl ester were synthesised as reported.[45] 2-{2-[2-(2-Azidoethoxy)ethoxy]ethyl methyl-sulfonate was prepared analogously to the procedure described by Tahtaoui et. al. for the $PEG_3$-derivative. Melting points (uncorrected) were determined on a Stuart Scientific SMP3 capillary melting point apparatus. $^1$H-NMR and $^{13}$C-NMR spectra were recorded on a Bruker ARX 300, and AMX 400 spectrometer, respectively. Mass spectrometry was performed using a Varian MAT 212 (EI=70 eV), a Bruker MALDI-TOF-MS Reflex IV (matrix: DHB) or a QUATTRO LCZ (Waters Micromass, Manchester, UK) spectrometer with a nanospray capillary inlet. Elemental analysis was realised by a Vario EL III analyser. All animal experiments were conducted in accordance with local institutional guidelines for the care and use of laboratory animals.

Cell Lines and Reagents

Human breast cancer cell line MCF-7 (ATCC-No. HTB-22) was cultured in RPMI 1640 (Invitrogen Corporation, San Diego, USA) supplemented with 10% fetal calf serum, penicillin and streptomycin. Cells were grown routinely in a monolayer culture at 37° C. in a 5% $CO_2$ humidified air atmosphere. Antibodies were murine IgGs and specific for the endothelin A receptor. Monoclonal endothelin 1 receptor antibody (clone 16) was from Pharmingen (BD, San Jose, USA), polyclonal $ET_AR$ antibody (N-15) was from Santa Cruz (Santa Cruz Biotechnology, Santa Cruz, Calif.).

Example 1

Synthesis of 4,5-Dimethoxy-3-{2-[2-(2-phthalimidoylethoxy)ethoxy]ethoxy}benzaldehyde[3]

A solution of 500 mg (2.75 mmol) 4,5-dimethoxy-3-hydroxybenzaldehyde and 860 µl (1.03 g, 5.50 mmol) 1,2-bis(2-chloroethoxy)ethane in 20 ml DMF was treated with 2.24 g (6.88 mmol) caesium carbonate and heated to 55° C. for 20 h. After cooling the mixture was poured into 100 ml of ice water and extracted with chloroform. The organic extracts were washed with 50 ml of water twice and with brine, dried over sodium sulfate and evaporated. The resulting yellow oil (3-{2-[2-(2-chloroethoxy)ethoxy]-ethoxy}-4,5-dimethoxybenzaldehyde, 730 mg, 2.20 mmol, 80%) and 414 mg (2.20 mmol) phthalimide potassium salt were dissolved in 25 ml of DMF and stirred at 50° C. for 68 h. After hydrolysis with 50 ml of ice water the mixture was extracted with chloroform, the combined organic phases were washed with water and brine and dried over sodium sulfate. Evaporation of the solvent yielded 932 mg of a yellow oil, which was purified by silica gel column chromatography (petroleum ether/ethyl acetate 1/1). The desired product accrued as a white powder (595 mg, 1.34 mmol, 61%). $^1$H-NMR (CDCl$_3$) δ=9.85 (s, 1H), 7.83 (m, 2H), 7.69 (m, 2H), 7.12 (m, 2H), 4.16 (m, 2H), 3.93 (s, 3H), 3.92 (s, 3H), 3.89 (m, 2H), 3.83 (m, 2H), 3.75 (m, 2H), 3.67 (m, 4H) ppm. $^{13}$C-NMR δ=190.9, 168.2, 153.8, 152.9, 144.4, 133.9, 132.2, 131.6, 123.2, 109.3, 106.6, 70.8, 70.3, 69.7, 69.0, 68.0, 61.0, 56.4, 37.3 ppm. MS: m/z=466 [M+Na]$^+$, 443 [M]$^+$. Anal. calcd for C$_{23}$H$_{25}$NO$_8$: C, 62.30, H, 5.68, N, 3.16. Found C, 61.97, H, 5.76, N, 3.10.

Example 2

Synthesis of 3-Benzo[1,3]dioxol-5-yl-5-hydroxy-5-(4-methoxyphenyl)-4-(4,5-dimethoxy-3-{2-[2-(2-phthalimidoylethoxy) ethoxy]ethoxy}benzyl)-5H-furan-2-one A mixture of 887 mg (2.00 mmol) 4,5-dimethoxy-3-{2-[2-(2-phthalimidoylethoxy)ethoxy]ethoxy}benzalde-hyde, 689 mg (2.10 mmol) 2-(1,3-benzodioxol-5-yl)-1-(4-methoxyphenyl)-4-oxobutyric acid methyl ester and 120 mg (2.20 mmol) sodium methoxide were dissolved in 20 ml of methanol at 0° C. and then heated to reflux for 12 h under an argon atmosphere. Acetic acid was added (1.0 ml) and the mixture was heated to reflux for another 6 h. After cooling down the mixture was poured into 50 ml of water and extracted with ethyl acetate. The combined organic extracts were washed successively with water and brine and dried over sodium sulfate. After evaporation of the solvent a yellow oil remained, which was purified by silica gel column chromatography (light petroleum/ethyl acetate 2/1; 1/1; 1/2). Yield: 800 mg (1.06 mmol, 53%). $^1$H-NMR (CDCl$_3$) δ=7.80 (m, 2H), 7.67 (m, 2H, 7.38 (m, 2H), 6.92 (m, 2H), 6.79 (m, 3H), 6.13 (d, 1H, J=2.0 Hz), 5.98 (d, 1H, J=2.0 Hz), 5.94 (s, 2H), 3.87 (m, 4H), 3.77 (s, 3H), 3.73 (m, 2H), 3.71 (s, 3H), 3.69 (m, 2H), 3.64 (m, 2H), 3.62 (s, 3H), 3.61 (s, 4H) ppm. The proton of the butenolide hydroxy group was not detected. $^{13}$C-NMR δ=171.1, 168.4, 160.4, 160.3, 153.0, 152.2, 148.1, 147.7, 143.7, 137.3, 134.0, 132.1, 131.8, 129.0, 128.2, 127.5, 123.3, 123.2, 123.1, 113.9, 109.5, 108.4, 108.2, 106.4, 101.3, 70.7, 70.2, 69.8, 68.6, 67.9, 60.7, 55.9, 55.3, 37.4, 32.1 ppm. MS: m/z=792 [M+K]$^+$, 776 [M+Na]$^+$, 753 [M]$^+$, 736 [M−OH]$^+$.

Example 3

Synthesis of 4,5-Dimethoxy-3-{2-[2-{2-azidoethoxy}ethoxy) ethoxy]ethoxy}benzaldehyde [5]

A mixture of 5.22 g (17.55 mmol) 2-{2-[2-(2-azidoethoxy) ethoxy]ethoxy)ethylmethylsulfonate, 3.20 g (17.55 mmol) 3,4-dimethoxy-5-hydroxybenzaldehyde and 11.50 g (35.20 mmol) caesium carbonate in 120 ml DMF is heated at 50° C. for 17 h. The mixture is poured into 100 ml saturated aqueous ammonium chloride solution and extracted with methylene chloride. The combined organic layers are washed with water and brine, dried over MgSO$_4$ and evaporated. The residue is purified by silica gel column chromatography (toluene/ethyl acetate 1/1), yielding 4.58 g (11.95 mmol, 68%) of the product as a clear yellow oil. $^1$H-NMR (CDCl$_3$) δ=9.77 (s, 1H), 7.09 (d, 1H, J=2.2 Hz), 706 (d, 1H, J=2.2 Hz), 4.17 (m, 2H), 3.88 (s, 3H), 3.85 (s, 3H), 3.83 (m, 2H), 3.66 (m, 2H), 3.60 (m, 8H), 3.30 (t, 2H, J=5.4 Hz) ppm. $^{13}$C-NMR δ=190.7, 153.6, 152.7, 144.2, 131.5, 109.0, 106.4, 70.7, 70.6, 70.5 (2 signals), 69.8, 69.5, 68.8, 60.8, 56.1, 50.5 ppm. MS: m/z=383 [M]$^+$. Anal. calcd for C$_{17}$H$_{25}$N$_3$O$_7$: C, 53.26, H, 6.57, N, 10.96. Found C, 53.15, H, 6.66, N, 10.99.

Example 4

Synthesis of 3-Benzo[1,3]dioxol-5-yl-5-hydroxy-5-(4-methoxyphenyl)-4-(4,5-dimethoxy-3-(2-{2-[2-(2-azidoethoxy) ethoxy]ethoxy}ethoxy)benzyl)-5H-furan-2-one[6]

A mixture of 1.16 g (3.00 mmol) 4,5-Dimethoxy-3-(2-{2-[2-(2-azidoethoxy)ethoxy]ethoxy}ethoxy)benz-aldehyde, 1.10 g (3.20 mmol) 2-(1,3-Benzodioxol-5-yl)-1-(4-methoxyphenyl)-4-oxobutyric acid methyl ester and 216 mg (4.00 mmol) sodium methoxide are dissolved in 20 ml of methanol at 0° C. and the heated to reflux for 15 h. Acetic acid is added (1.5 ml) and the mixture is heated to reflux for further 5 h under an argon atmosphere. After cooling down the mixture is poured into 50 ml of water and extracted with ethyl acetate. The combined organic extracts are washed successively with water and brine and dried over sodium sulfate. After evaporation of the solvent a yellow oil remains, which is purified by silica gel column chromatography (diisopropyl ether/acetone 3/1). Yield: 1.49 g (2.15 mmol, 72%). $^1$H-NMR (CDCl$_3$) δ=7.60 (m, 2H), 7.13, (m, 2H), 7.03 (m, 3H), 6.25 (s, 1H), 6.22 (s, 1H), 6.17 (s, 2H), 4.17 (m, 2H), 4.00 (s, 3H), 3.96 (s, 3H), 3.94-3.80 (m, 17H), 3.57 (m, 2H) ppm. The proton of the butenolide hydroxy group was not detected. $^{13}$C-NMR δ=171.0, 160.4, 160.3, 153.0, 152.1, 148.1, 147.7, 137.2, 131.7, 128.9, 128.1, 127.4, 123.1, 123.0, 113.9, 109.4, 108.3, 108.1, 106.3, 105.7, 101.3, 70.6 (2 signals), 70.5, 69.9, 69.7, 68.6, 68.4, 60.7, 55.9, 55.3, 50.6, 32.0 ppm. MS: m/z=732 [M+K]$^+$, 716 [M+Na]$^+$, 693 [M]$^+$, 676 [M−OH]$^+$, 668 [M−N$_2$]$^+$. Anal. calcd for C$_{35}$H$_{39}$N$_3$O$_{12}$: C, 60.60, H, 5.67, N, 6.06. Found C, 60.50, H, 5.90, N, 5.69.

Example 5

Synthesis of 3-Benzo[1,3]dioxol-5-yl-5-hydroxy-5-(4-methoxyphenyl)-4-(4,5-dimethoxy-3-(2-{2-[2-(2-aminoethoxy) ethoxy]ethoxy}ethoxy)benzyl)-5H-furan-2-one[7]

A mixture of 1.49 g (2.15 mmol) of 6 and 1.00 g (≈3.00 mmol) of polymer bound PPh$_3$ (polystyrene, 2% DVB, FLUKA) is suspended in 10 ml of THF and stirred at rt overnight. Water is added (200 μl, ≅10 mmol) and stirring is continued for 3 d. The polymer is removed by filtration and the filtrate is evaporated in vacou. The remaining oil is purified by silica gel column chromatography (EtOAc/MeOH/NEt$_3$ 500/100/30), yielding 635 mg of the product (0.95 mmol, 44%). $^1$H-NMR (CDCl$_3$) δ=7.32 (d, 2H, $^3$J=8.1 Hz), 6.83, (m, 2H), 6.75 (d, 2H, $^3$J=8.1 Hz), 6.68 (d, 1H, 3J=7.7 Hz), 6.14 (s, 1H), 5.91 (s, 1H), 5.85 (s, 2H), 3.88 (m, 2H), 3.70 (s, 4H), 3.64 (s, 3H), 3.59 (m, 4H), 3.54 (s, 3H), 3.48 (m, 4H) 3.37 (m, 2H), 3.15 (m, 2H) ppm. The protons of the butenolide hydroxy group and the amino function were not detected. $^{13}$C-NMR δ=171.2, 160.8, 160.1, 152.8, 151.9, 147.9, 147.5, 137.3, 131.8, 129.2, 127.8, 127.4, 123.2, 123.1, 113.7, 109.4, 108.5, 108.2, 106.6, 106.0, 101.2, 70.6, 70.4, 70.3, 70.2, 69.8, 69.7, 68.6, 60.6, 55.8, 55.2, 40.0, 32.0 ppm. MS: m/z=690 [M+Na]$^+$, 668 [M+H]$^+$.

Example 6

Tissue Preparation

Microsomes were prepared by homogenizing ventricles from DBA mice at 4° C. for 90 seconds in 1 ml of buffer A (10 mM EDTA, 10 mM HEPES, 0.1 mM benzamidine, pH 7.4), using a Polytron PT 3000 (Kinematica, Luceme, Switzerland). Homogenates were centrifuged at 45,000× $g_{max}$ for 15 min at 4° C. The pellets were resuspended in 1 ml of buffer B (1 mM EDTA, 10 mM HEPES, 0.1 mM benzamidine, pH 7.4) and recentrifuged at 45,000× $g_{max}$ for 15 min at 4° C. The pellets were resuspended in 1 ml of buffer B and centrifuged at 10,000× $g_{max}$ for 10 min at 4° C. The supernatants were recentrifuged at 45,000×$g_{max}$ for 15 min at 4° C. The pellets, partially enriched membranes, were resuspended in buffer C (50 mM Tris.HCl, 5 mM $MgCl_2$, pH 7.4), and stored frozen at −80° C.

Example 7

Competition Binding Studies

For competition binding studies, the prepared membranes were resuspended in buffer D (10 mM Tris.HCl, 154 mM NaCl, 0.1 mM ascorbic acid, pH 7.4) at 0° C. 10 μg of membranes were incubated with a constant concentration of [$^{125}$I]ET-1 (40 pM) and with varying concentrations (10 pM-100 μM) of ET antagonist 4 at 37° C. for 4 h. Reactions were stopped by filtering onto Whatman GF/B filters and washed with 0.9% NaCl at 4° C. The membrane bound radioactivity was determined in a γ-scintillation counter. Competition binding curves were analyzed by nonlinear regression analysis using the XMGRACE programme (Linux software). Cells were seeded in 4-well plates (Nunc, Wiesbaden) and incubated in culture medium (0.5 ml/well) overnight. For binding studies cells were washed twice with PBS and resuspended in 150 μl binding-buffer (20 mM HEPES in PBS with $Ca^{2+}/Mg^{2+}$, 0.2% BSA, 0.1% Glucose, pH 7.4). Cy 5.5 (final amount 5 nmol) or $ET_AR$-CY 5.5 (5.5 nmol) was added into each well. After an incubation period of 45 min at 4° C. cells were washed twice with PBS and were resuspended in binding buffer. For competition binding studies free $ET_AR$ antagonist (final amount 50 nmol) or $ET_AR$ antibodies (1.3 μg) were added to each well for 45 min at 4° C. Cells could be directly visualized by fluorescence microscopy (40× and 60× objective, Nikon TE 2000-S, Nikon-Düsseldorf). The microscope was equipped with a mercury vapour lamp (100 W), 620/775 nm and 545/675 nm (excitation/emission) filters (AHF Analysentechnik, Tübingen), a Nikon DXM1200F camera and ACT1/DXM1200F software (Nikon, Japan).

Example 8

Fluorochrome Conjugation

The amino functionalised derivative 7 (≅1.0 mg, 1.5 μmol) was dissolved in 100 μl of DMSO and 400 μl of a bicarbonate buffer (0.1 M $NaHCO_3$, pH 8.6). To this was added a solution of Cy 5.5 NHS-ester (≅1.6 mg, 1.4 μmol) or FITC isomer 1 (0.6 mg, 1.5 μmol) in 300 μl DMSO. The solution was stirred for 1 h at rt in the dark and stored at −20° C.

Example 9

Synthesis of Model and Precursor Compounds

The synthesis of the butenolide compounds 4,6 and 7 was accomplished via the route outlined in FIG. 1. Ketoester 1 was synthesised as described by Patt et. al. by subsequent Aldol condensation, Michael addition and nitrile hydrolysis/esterification. Benzaldehyde 3 was accessible by reaction of 3,4-dimethoxy-5-hydroxybenzaldehyde with 1,2-bis(2-chloroethoxy)ethane and caesium carbonate in DMF. We found that the use of caesium-instead of potassium carbonate allows to perform the substitution reactions of these phenolic alcohols with nucleophiles at lower temperatures, thereby improving the yield of the desired ethers. Final addition of potassium phthalimide gives the product in 70% yield.

The synthesis of benzaldehyde 5 started with the preparation of the PEG-spacer. This was conducted in accordance to the procedure described by Tahtaoui et. al. for the corresponding $PEG_3$-derivative. Subsequent reaction of triphenylmethanol and methanesulfonyl chloride with tetraethylene glycol yields the trityl protected, activated PEG derivative X, which is further converted to the azide Y by reaction with sodium azide in acetonitrile at reflux. The trityl group is then removed by action of TsOH in methanol, and the free hydroxy function was similarly activated with methanesulfonyl chloride. The coupling of the so modified PEG spacer 2 to 3,4-dimethoxy-5-hydroxybenzaldehyde is done by reaction of the compounds and caesium carbonate in DMF at 80° C. for 4 h.

The final step includes the reaction of the ketoester 1 with the corresponding aldehyde. This is carried out by subsequently adding the ketoester and the aldehyde to a solution of sodium methylate in methanol at 0° C. and then refluxing the mixture for 12-15 h under an inert atmosphere (argon). Finally, the addition of acetic acid and another 5-6 h reflux is necessary to obtain the ring-closed butenolide products.

Compound 6 is then converted to the free amine by staudinger reaction with triphenylphosphine and water in thf. In this special case we used polymer bound triphenylphosphine (polystyrene, 2% DVB) to remove the resulting oxides more easily.

Example 10

In vitro Assays

The affinity of the prepared butenolide derivative 4 towards endothelin receptors was determined by competition binding studies using [$^{125}$I]ET-1 (PerkinElmer Live Sciences Inc., Billerica, Mass., USA) and mouse ventricular membrane preparations. The binding of [$^{125}$I]ET-1 to ventricular membranes was specific, saturable and of high affinity. Scatchard[46,47] transformation of the saturation data yielded values for the dissociation constant ($K_D$±208±2 pM) and the maximum number of binding sites ($B_{max}$=300±3 fmol/mg protein). Different concentrations of the prepared compound (1.0 pM-100 μM) were incubated with 40 pM [$^{125}$I]ET-1 and a fixed amount of mouse ventricular membrane preparation (10 μg) at 37° C. for 4 h. The membrane bound radioactivity was evaluated using a γ-scintillation counter and standardized on percentage of [$^{125}$I]ET-1. The Competition binding curves were fitted by non-linear regression analysis using the XMGRACE program (Linux software).

The receptor affinity of 4 is comparable to that of the lead compound. We found an $IC_{50}$-value of 8.4±1.7 nM for the model compound 4 and a value of 2.2±0.5 nM for the lead compound PD 156707, which was used in this essay for comparison (lit. 0.3 nM).

Example 11

Fluorochrome Conjugation

The amino functionalised compound 7 was used for the conjugation of cyanine dye Cy 5.5 (as NHS-ester) and fluorescein (as FITC). The reactions were carried out similar to usual peptide labelling procedures, using an aqueous bicarbonate buffer and DMSO. In case of the FITC-conjugate the product was purified by reversed phase HPLC, whilst the Cy 5.5-conjugate was used without further purification, HPLC analysis indicated 90% purity. The identification of the labelled ligands was possible by mass spectrometry.

Example 12

In Vitro Binding Assays

We tested the specific visualization of the $ET_A$ receptor on positive MCF-7 human breast adenocarcinoma cells with the fluorochrome conjugated ligand 9. Binding of the labelled antagonist could be directly analyzed by fluorescence microscopy. Negligible signals were detected with the MCF-7 cells when incubated with non modified Cy 5.5 dye (5 nmol, data not shown). Incubation of the cells with 5.5 nmol 9 lead to a specific visualization of the $ET_A$ receptor. The signal was distributed over the cell surface and membrane-associated. Blocking of the signal was possible with a tenfold concentration of unlabeled $ET_AR$ antagonist PD 156707 (50 nmol) or with 1,3 μg of the $ET_A$ receptor specific antibodies (s FIG. 1). At higher concentrations of the conjugate and the unlabelled antagonist (up to 100 nmol) cells detached from the bottom of the flask and showed an unspecific uptake of the labelled conjugate with staining of the nuclear region.

Example 13

In Vivo Binding Assays

Here we characterised a recently synthesised $ET_A$ receptor affine non peptidic near infrared fluorescent photoprobe ($ET_AR$-CY 5.5) in vitro and in vivo. While in vitro cell binding assays showed high amounts of cellular fluorescence in $ET_AR$-positive MCF-7 cells, $ET_AR$-negative MDA-MB 435 cells showed little to no cellular fluorescence confirming corresponding western blot analyses. Binding of $ET_AR$-Cy 5.5 could be blocked by predosing with a corresponding anti-$ET_AR$ antibody or non-peptidic $ET_AR$ antagonists PD 156707 (FIG. 7). In vivo imaging of tumor xenografts by FRI and FMT (2 nmol $ET_AR$-Cy 5.5 i.v.) showed high fluorescence signal yields for both MDA-MB 435 and MCF-7 xenografts (FIG. 8). The evaluation of the FMT-data and the biodistribution are depicted in the following tables.

| Evaluation of the FMT-data: ETAR-Cy 5.5 for MDA-MB-435 | | | | | |
|---|---|---|---|---|---|
| MDA-MB-435 | mean | std | pmol | std | mice |
| nativ | | | | | |
| 1 h | 356.89 | 83.12 | 40.56 | 45.76 | 9 |
| 3 h | 326.33 | 76.18 | 27.67 | 18.37 | 7 |
| 5 h | 418.17 | 64.15 | 55.50 | 56.00 | 6 |
| 24 h | 444.38 | 54.51 | 63.57 | 65.23 | 7 |
| block | | | | | |
| 1 h | 253.57 | 172.54 | 22.14 | 22.99 | 7 |
| 3 h | 323.25 | 103.12 | 17.25 | 7.41 | 8 |
| 5 h | 343.78 | 139.69 | 19.67 | 16.73 | 9 |
| 24 h | 273.80 | 147.99 | 34.80 | 22.60 | 8 |

| Evaluation of the FMT-data: ETAR-Cy 5.5 for MCF-7 | | | | | |
|---|---|---|---|---|---|
| MCF-7 | mean | std | pmol | std | mice |
| nativ | | | | | |
| 1 h | 148.00 | 35.03 | 599.00 | 181.25 | 3 |
| 3 h | 79.00 | #DIV/0! | 339.00 | #DIV/0! | 1 |
| 5 h | 115.50 | 53.03 | 473.00 | 203.65 | 2 |
| 24 h | 207.67 | 240.15 | 33.00 | 41.57 | 3 |
| block | | | | | |
| 1 h | 196.50 | 136.47 | 224.00 | 264.46 | 2 |
| 3 h | 66.50 | 26.16 | 274.50 | 112.43 | 2 |
| 5 h | 100.67 | 56.05 | 201.67 | 202.95 | 3 |
| 24 h | 125.50 | 51.62 | 9.00 | 2.83 | 2 |

| Biodistribution of EtAR_MDA-MB-435 | | | | | |
|---|---|---|---|---|---|
| with block (2) | | | nativ (5) | | |
| heart | tumor | spleen | heart | tumor | spleen |
| 214.33 | 4201.32 | 236.20 | 224.76 | 5332.69 | 252.73 |
| 6.91 | 309.49 | 9.22 | 53.94 | 1938.03 | 56.30 |
| lung | kidney | liver | lung | kidney | liver |
| 515.09 | 322.18 | 642.69 | 580.60 | 333.14 | 666.91 |
| 280.12 | 87.82 | 221.42 | 167.91 | 74.29 | 152.93 |

The in vivo binding specificity could be verified by predosing experiments with unmodified $ET_AR$ antagonist, which resulted in a significant decrease of tumor fluorescence. Protein expression analysis of whole tumor tissue revealed that in MDA-MB 435 cells mainly murine (e.g. derived from endothelial cells) $ET_AR$ is present while MCF-7 tumor xenografts express both the human and murine form of $ET_AR$.

This leads to the conclusion that in vivo $ET_A$ receptor imaging is feasible using an $ET_A$ receptor affine non peptidic near infrared fluorescent photoprobe ($ET_AR$-Cy 5.5). This imaging paradigm maybe helpful for non-invasive chraracterisation of breast tumor tissues and may thus facilitate patient selection for novel $ET_AR$ antogonist therapies. In tumor xenograft models $ET_AR$-Cy 5.5 can visualise both the $ET_AR$ expression of host (e.g. of endothelial cells) and of tumor tissue.

Example 14

Materials and methods. All chemicals, reagents and solvents for the synthesis of the compounds were analytical grade and purchased from commercial sources. PD 156707 and 2-(benzo-[1,3]-dioxol-5-yl)-1-(4-benzyloxyphenyl)-4-oxobutyric acid methyl ester 3 were synthesised as reported (37). 2-{2-[2-(2-azidoethoxy)ethoxy]ethoxy)ethyl methanesulfonate was prepared according to the procedure described by Tahtaoui et. al. for the $PEG_3$-derivative (38). Melting points (uncorrected) were determined on a Stuart Scientific SMP3 capillary melting point apparatus. $^1$H-NMR and $^{13}$C-NMR spectra were recorded on a Bruker ARX 300, an AMX 400 (Bruker BioSpin GmbH, Rheinstetten, Germany) or a Varian 500 MHz INOVA spectrometer (Varian Deutschland GmbH, Darmstadt, Germany), respectively. Mass spectrometry was performed using a Varian MAT 212 (EI=70 eV, Varian Deutschland GmbH, Darmstadt, Germany), a Bruker MALDI-TOF-MS Reflex IV (matrix: DHB, Bruker Daltonics GmbH, Bremen, Germany) or a QUATTRO LCZ (Waters Micromass, Manchester, UK) spectrometer with a nanospray capillary inlet. Elemental analysis was realised by a Vario EL III analyser (Elementar Analysensysteme GmbH, Hanau, Germany).

Cell lines and reagents. Human breast adenocarcinoma cell line MCF-7 (ATCC-No. HTB-22), MDA-MB-435 human breast carcinoma cells (ATCC-No. HTB-123) and HT-1080 human fibrosarcoma cells (ATCC-No. CCL-121) were cultured in RPMI 1640 (Invitrogen Corporation, San Diego, USA) supplemented with 10% fetal calf serum, penicillin and streptomycin. Cells were grown routinely in a monolayer culture at 37° C. in a 5% $CO_2$ humidified air atmosphere. Polyclonal $ET_AR$ antibody (N-15) was from Santa Cruz (Santa Cruz Biotechnology, Santa Cruz, Calif., USA).

Synthetic Organic Chemistry 4,5-Dimethoxy-3-{2-[2-(2-phthalimidoylethoxy) ethoxy]ethoxy}benzaldehyde 2

A solution of 500 mg (2.75 mmol) 4,5-dimethoxy-3-hydroxybenzaldehyde 1 and 860 µl (1.03 g, 5.50 mmol) 1,2-bis(2-chloroethoxy)ethane in 20 ml DMF was treated with 2.24 g (6.88 mmol) caesium carbonate and heated to 55° C. for 20 hrs. After cooling the mixture was poured into 100 ml of ice water and extracted with chloroform. The organic extracts were washed twice with 50 ml of water and with brine, dried over sodium sulfate and evaporated. The resulting yellow oil was flash-chromatographed (petroleum ether/ethyl acetate 2/1) to yield 3-{2-[2-(2-chloroethoxy)ethoxy]ethoxy}-4,5-dimethoxybenzaldehyde (730 mg, 2.20 mmol, 80%), which was directly used for the next synthesis step.

The residue from the above step and 414 mg (2.20 mmol) phthalimide potassium salt were dissolved in 25 ml of DMF and stirred at 50° C. for 68 hrs. After hydrolysis with 50 ml of ice water the mixture was extracted with chloroform, the combined organic phases were washed with water and brine and dried over sodium sulfate. Evaporation of the solvent yielded 932 mg of a yellow oil, which was purified by silica gel column chromatography (petroleum ether/ethyl acetate 1/1). The desired product accrued as a colourless oil (595 mg, 1.34 mmol, 61%). $^1$H-NMR (CDCl$_3$) δ=9.85 (s, 1H), 7.83 (m, 2H), 7.69 (m, 2H), 7.12 (m, 2H), 4.16 (m, 2H), 3.93 (s, 3H), 3.92 (s, 3H), 3.89 (m, 2H), 3.83 (m, 2H), 3.75 (m, 2H), 3.67 (m, 4H) ppm. $^{13}$C-NMR δ=190.9, 168.2, 153.8, 152.9, 144.4, 133.9, 132.2, 131.6, 123.2, 109.3, 106.6, 70.8, 70.3, 69.7, 69.0, 68.0, 61.0, 56.4, 37.3 ppm. MS: m/z=466 [M+Na]$^+$, 443 [M]$^+$. Anal. calcd for C$_{23}$H$_{25}$NO$_8$: C, 62.30, H, 5.68, N, 3.16. Found C, 61.97, H, 5.76, N, 3.10.

3-Benzo[1,3]dioxol-5-yl-4-(4,5-dimethoxy-3-{2-[2-(2-phthalimidoylethoxy)ethoxy]ethoxy}-benzyl)-5-hydroxy-5-(4-methoxyphenyl)-5H-furan-2-one 4

A mixture of 887 mg (2.00 mmol) 4,5-dimethoxy-3-{2-[2-(2-phthalimidoylethoxy)ethoxy]ethoxy}benzaldehyde 2, 689 mg (2.10 mmol) 2-(benzo-[1,3]-dioxol-5-yl)-1-(4-benzyloxyphenyl)-4-oxobutyric acid methyl ester 3 and 120 mg (2.20 mmol) sodium methoxide were dissolved in 20 ml of methanol at 0° C. and then heated to reflux for 12 hrs under an argon atmosphere. Acetic acid was added (1.0 ml) and the mixture was heated to reflux for another 6 hrs. After cooling to room temperature the mixture was poured into 50 ml of water and extracted with ethyl acetate. The combined organic extracts were successively washed with water and brine and dried over sodium sulfate. After evaporation of the solvent a yellow oil remained which was purified by silica gel column chromatography (petroleum ether/ethyl acetate 2/1>1/1>1/2). Yield: 800 mg (1.06 mmol, 53%). $^1$H-NMR (CDCl$_3$) δ=7.80 (m, 2H), 7.67 (m, 2H, 7.38 (m, 2H), 6.92 (m, 2H), 6.79 (m, 3H), 6.13 (d, 1H, J=2.0 Hz), 5.98 (d, 1H, J=2.0 Hz), 5.94 (s, 2H), 3.87 (m, 4H), 3.77 (s, 3H), 3.73 (m, 2H), 3.71 (s, 3H), 3.69 (m, 2H), 3.64 (m, 2H), 3.62 (s, 3H), 3.61 (s, 4H) ppm. The proton of the butenolide hydroxy group was not detected. $^{13}$C-NMR δ=171.1, 168.4, 160.4, 160.3, 153.0, 152.2, 148.1, 147.7, 143.7, 137.3, 134.0, 132.1, 131.8, 129.0, 128.2, 127.5, 123.3, 123.2, 123.1, 113.9, 109.5, 108.4, 108.2, 106.4, 101.3, 70.7, 70.2, 69.8, 68.6, 67.9, 60.7, 55.9, 55.3, 37.4, 32.1 ppm. MS: m/z=792 [M+K]$^+$, 776 [M+Na]$^+$, 753 [M]$^+$, 736 [M−OH]$^+$. HRMS: Calcd. for C$_{41}$H$_{39}$NO$_{13}$Na$^+$ 776.2314, found 776.2303.

3-{2-[2-(2-{2-Azidoethoxy}ethoxy)ethoxy]ethoxy}-4,5-dimethoxybenzaldehyde 8

A mixture of 5.22 g (17.55 mmol) 2-{2-[2-(2-azidoethoxy)ethoxy]ethoxy}ethyl methanesulfonate 7, 3.20 g (17.55 mmol) 3,4-dimethoxy-5-hydroxybenzaldehyde 1 and 11.5 g (35.20 mmol) caesium carbonate in 120 ml DMF was heated at 50° C. for 17 hrs. The mixture was poured into 100 ml saturated aqueous ammonium chloride solution and extracted with methylene chloride. The combined organic layers were washed with water and brine, dried over MgSO$_4$ and evaporated. The residue was purified by silica gel column chromatography (toluene/ethyl acetate 1/1), yielding 4.58 g (11.95 mmol, 68%) of the product as a clear yellow oil. $^1$H-NMR (CDCl$_3$) δ=9.77 (s, 1H), 7.09 (d, 1H, J=2.2 Hz), 7.06 (d, 1H, J=2.2 Hz), 4.17 (m, 2H), 3.88 (s, 3H), 3.85 (s, 3H), 3.83 (m, 2H), 3.66 (m, 2H), 3.60 (m, 8H), 3.30 (t, 2H, J=5.4 Hz) ppm. $^{13}$C-NMR δ=190.7, 153.6, 152.7, 144.2, 131.5, 109.0, 106.4, 70.7, 70.6, 70.5 (2 signals), 69.8, 69.5, 68.8, 60.8, 56.1, 50.5 ppm. MS: m/z=383 [M]$^+$. Anal. calcd for C$_{17}$H$_{25}$N$_3$O$_7$: C, 53.26, H, 6.57, N, 10.96. Found C, 53.15, H, 6.66, N, 10.99.

3-Benzo[1,3]dioxol-5-yl-4-(3-(2-{2-[2-(2-azidoethoxy)ethoxy]ethoxy}ethoxy)-4,5-dimethoxybenzyl)-5-hydroxy-5-(4-methoxyphenyl)-5H-furan-2-one 9

A mixture of 1.16 g (3.00 mmol) 3-(2-{2-[2-(2-azidoethoxy)ethoxy]ethoxy}ethoxy)-4,5-dimethoxybenzaldehyde 8, 1.10 g (3.20 mmol) 2-(1,3-benzodioxol-5-yl)-1-(4-methoxyphenyl)-4-oxobutyric acid methyl ester 3 and 216 mg (4.00 mmol) sodium methoxide in 20 ml of methanol is heated to reflux for 15 hrs under an argon atmosphere. Acetic acid was added (1.5 ml) and the mixture was heated to reflux for further 5 hrs. After cooling the mixture was poured into 50 ml of water and extracted with ethyl acetate. The combined organic extracts were successively washed with water and brine and dried over sodium sulfate. After evaporation of the solvent a yellow oil remained, which was purified by silica gel column chromatography (diisopropyl ether/acetone 3/1). Yield: 1.49 g (2.15 mmol, 72%). $^1$H-NMR (CDCl$_3$) δ=7.60 (m, 2H), 7.13, (m, 2H), 7.03 (m, 3H), 6.25 (s, 1H), 6.22 (s, 1H), 6.17 (s, 2H), 4.17 (m, 2H), 4.00 (s, 3H), 3.96 (s, 3H), 3.94-3.80 (m, 17H), 3.57 (m, 2H) ppm. The proton of the butenolide hydroxy group was not detected. $^{13}$C-NMR δ=171.0, 160.4, 160.3, 153.0, 152.1, 148.1, 147.7, 137.2, 131.7, 128.9, 128.1, 127.4, 123.1, 123.0, 113.9, 109.4, 108.3, 108.1, 106.3, 105.7, 101.3, 70.6 (2 signals), 70.5, 69.9, 69.7, 68.6, 68.4, 60.7, 55.9, 55.3, 50.6, 32.0 ppm. MS: m/z=732 [M+K]$^+$, 716 [M+Na]$^+$, 693 [M]$^+$, 676 [M−OH]$^+$, 668

[M−N$_2$]$^+$. Anal. calcd for C$_{35}$H$_{39}$N$_3$O$_{12}$: C, 60.60, H, 5.67, N, 6.06. Found C, 60.50, H, 5.90, N, 5.69.

3-Benzo[1,3]dioxol-5-yl-4-(3-{2-[2-(2-aminoethoxy)ethoxy]ethoxy}ethoxy)-4,5-dimethoxybenzyl)-5-hydroxy-5-(4-methoxyphenyl)-5H-furan-2-one 10

A mixture of 1.49 g (2.15 mmol) of 3-Benzo[1,3]dioxol-5-yl-4-(3-(2-{2-[2-(2-azidoethoxy)ethoxy]ethoxy}ethoxy)-4,5-dimethoxybenzyl)-5-hydroxy-5-(4-methoxyphenyl)-5H-furan-2-one 9 and 1.00 g (3.00 mmol) of polymer bound PPh$_3$ (polystyrene, 2% DVB, FLUKA) was suspended in 10 ml of THF and stirred at room temperature overnight. Water is added (200 μl, ≈10 mmol) and stirring was continued for 3 d. The polymer was removed by filtration and the filtrate was evaporated in vacuo. The remaining oil was purified by silica gel column chromatography (EtOAc/MeOH/NEt$_3$ 5/1/0.3), yielding 246 mg of the product (0.37 mmol, 17%). $^1$H-NMR (CDCl$_3$) δ=7.32 (d, 2H, J=8.1 Hz), 6.83, (m, 2H), 6.75 (d, 2H, J=8.1 Hz), 6.68 (d, 1H, J=7.7 Hz), 6.14 (s, 1H), 5.91 (s, 1H), 5.85 (s, 2H), 3.88 (m, 2H), 3.70 (s, 4H), 3.64 (s, 3H), 3.59 (m, 4H), 3.54 (s, 3H), 3.48 (m, 4H) 3.37 (m, 2H), 3.15 (m, 2H) ppm. The protons of the butenolide hydroxy group and the amino function were not detected. $^{13}$C-NMR δ=171.2, 160.8, 160.1, 152.8, 151.9, 147.9, 147.5, 137.2, 131.8, 129.2, 127.8, 127.4, 123.2, 123.1, 113.7, 109.4, 108.5, 108.2, 106.6, 106.0, 101.2, 70.6, 70.4, 70.3, 70.2, 69.8, 69.7, 68.6, 60.6, 55.8, 55.2, 40.0, 32.0 ppm. MS: m/z=690 [M+Na]$^+$, 668 [M+H]$^+$. Elemental or HRMS analysis could not be obtained from this product.

2-(3-{2-[2-(2-{2-Azidoethoxy}ethoxy)ethoxy]ethoxy}-4,5-dimethoxyphenyl)-1,3-dioxolane 11

A mixture of 4.95 g (12.91 mmol) 3-{2-[2-(2-{2-azidoethoxy}ethoxy)ethoxy]ethoxy}-4,5-dimethoxybenzaldehyde 8, 5 ml (5.57 g, 90 mmol) ethylene glycol and 200 mg (1.0 mmol) p-toluene sulfonic acid monohydrate was refluxed in 120 ml of toluene for 8 hrs using a Dean-Stark trap. After cooling to room temperature the rection mixture was poured into 200 ml of diluted sodium bicarbonate solution, washed with water and brine and dried over magnesium sulfate. After removal of the solvent the residue was purified by silica gel column chromatography (cyclohexane/ethyl acetate 1/1), giving 4.43 g (10.8 mmol, 80%) of the product as a clear oil. $^1$H-NMR (CDCl$_3$) δ=6.73 (dd, 2H, J=5.0 Hz, J=1.8 Hz), 5.72 (s, 1H), 4.19 (m, 2H), 4.11 (m, 2H), 4.03 (m, 2H), 3.87 (s, 3H), 3.84 (s, 3H), 3.76-3.71 (m, 4H), 3.70-3.64 (m, 8H), 3.37 (m, 2H) ppm. $^{13}$C-NMR δ=153.3, 152.4, 139.2, 133.1, 105.4, 103.6, 103.4, 70.7, 70.6, 70.5 (2 peaks), 69.9, 69.6, 68.7, 65.1, 60.6, 56.0, 50.6 ppm. MS: m/z=427 [M]$^+$. Anal. calcd for C$_{19}$H$_{29}$N$_3$O$_8$: C, 53.39, H, 6.84, N, 9.83. Found C, 52.30, H, 6.89, N, 9.72.

2-(3-{2-[2-(2-{2-Aminoethoxy}ethoxy)ethoxy]ethoxy}-4,5-dimethoxyphenyl)-1,3-dioxolane 12

Fifty mg of Pd/C was added to a solution of 7.18 g (16.8 mmol) 2-(3-{2-[2-(2-{2-azidoethoxy}ethoxy)ethoxy]ethoxy}-4,5-dimethoxyphenyl)-1,3-dioxolane 11 in 100 ml ethanol. The mixture was stirred at ambient temperature under a hydrogen atmosphere overnight, filtered and purified by silica gel column chromatography to give 5.69 g (14.2 mmol, 84%) of the product as a clear oil. $^1$H-NMR (CDCl$_3$) δ=6.73 (dd, 2H, J=5.2 Hz, J=1.7 Hz), 5.72 (s, 1H), 4.19 (m, 2H), 4.11 (m, 2H), 4.02 (m, 2H), 3.86 (s, 3H), 3.84 (s, 3H), 3.87-3.85 (m, 2H), 3.75-3.69 (m, 2H), 3.69-3.59 (m, 6H), 3.57 (t, 1H, J=5.4 Hz), 3.49 (t, 1H, J=5.4 Hz), 2.84 (t, 1H, J=5.2 Hz), 2.79 (t, 1H, J=5.2 Hz), 1.74 (br, 2H) ppm. $^{13}$C-NMR δ=153.2, 152.3, 139.1, 133.0, 105.3, 103.5, 103.3, 73.2, 70.6, 70.5, 70.4, 70.1, 69.5, 68.6, 65.0, 60.5, 55.9, 41.6 ppm. MS: m/z=424 [M+Na]$^+$, 402 [M+H]$^+$. HRMS: Calcd. for C$_{19}$H$_{32}$NO$_8^+$ 402.2122, found 402.2122.

N-Boc-2-(3-{2-[2-(2-{2-Aminoethoxy}ethoxy)ethoxy]ethoxy}-4,5-dimethoxyphenyl)-1,3-dioxolane 13

A solution of 4.27 g (10.0 mmol) 2-(3-{2-[2-(2-{2-aminoethoxy}ethoxy)ethoxy]ethoxy}-4,5-dimethoxyphenyl)-1,3-dioxolane 12 and 1.66 ml (12.0 mmol) triethylamine in 50 ml methylene chloride was cooled in an ice bath. 2.40 g (11.0 mmol) di-tert-butyl dicarbonate was dissolved in 20 ml of methylene chloride and added dropwise. The mixture was warmed to room temperature and stirred overnight. After evaporation of the solvent the residue was purified by silica gel column chromatography (cyclohexane/ethyl acetate 1/2), yielding 2.51 g (5.0 mmol, 50%) of the product as a clear oil. $^1$H-NMR (CDCl$_3$) δ=6.73 (dd, 2H, J=4.3 Hz, J=1.7 Hz), 5.73 (s, 1H), 5.07 (br, 1H), 4.20 (m, 2H), 4.12 (m, 2H), 4.03 (m, 2H), 3.87 (s, 3H), 3.84 (s, 3H), 3.74 (m, 2H), 3.70-3.60 (m, 8H), 3.53 (t, 2H, J=5.3 Hz), 3.30 (m, 2H), 1.44 (s, 9H) ppm. $^{13}$C-NMR δ=153.9, 153.2, 152.3, 139.0, 133.0, 105.1, 103.6, 103.4, 79.0, 70.7, 70.5, 70.4, 70.1, 70.0, 69.6, 68.6, 65.1, 60.6, 56.0, 40.3, 28.3 ppm. MS: m/z=501 [M]$^+$, 444 [M-C$_4$H$_9$]$^+$. Anal. calcd for C$_{24}$H$_{39}$NO$_{10}$: C, 57.47, H, 7.84, N, 2.79. Found C, 57.25, H, 7.94, N, 2.79.

N-Boc-3-{2-[2-(2-{2-Aminoethoxy}ethoxy)ethoxy]ethoxy}-4,5-dimethoxybenzaldehyde 14

A solution of 2.00 g (3.99 mmol) N-Boc-2-(3-{2-[2-(2-{2-aminoethoxy}ethoxy)ethoxy]ethoxy}-4,5-dimethoxyphenyl)-1,3-dioxolane 13 in 50 ml of acetone was treated with iodine (100 mg, 10% n/n) and stirred at room temperature for 60 minutes. Acetone was removed and replaced by ethyl acetate. The organic phase was washed with diluted sodium thiosulfate solution, water and brine and dried over magnesium sulfate. After removal of the solvent 1.17 g (3.74 mmol, 94%) of a slightly yellow oil remains. $^1$H-NMR (CDCl$_3$) δ=9.85 (s, 1H), 7.16 (d, 1H, J=1.8 Hz), 7.13 (d, 1H, J=1.8 Hz), 5.00 (br, 1H), 4.25 (m, 2H), 3.95 (s, 3H), 3.92 (s, 3H), 3.89 (m, 2H), 3.74 (m, 2H), 3.70-3.59 (m, 6H), 3.53 (t, 2H, J=5.0 Hz), 3.30 (t, 2H, J=5.0 Hz), 1.44 (s, 9H) ppm. $^{13}$C-NMR δ=144.3, 131.6, 109.1, 106.6, 79.1, 70.8, 70.6, 70.5, 70.2, 70.1, 69.6, 69.0, 60.9, 56.2, 40.5, 28.3 ppm. MS: m/z=480 [M+Na]$^+$, 358 [M-(COOtBuH$_2$)]$^+$. HRMS: Calcd. for C$_{22}$H$_{35}$NO$_9$Na$^+$ 480.2204, found 480.2203.

N-Boc-3-Benzo[1,3]dioxol-5-yl-3-(2-{2-[2-(2-aminoethoxy)ethoxy]ethoxy}ethoxy)-4,5-dimethoxybenzyl)-5-hydroxy-5-(4-methoxyphenyl)-5H-furan-2-one 15

A solution of 5.76 g (12.6 mmol) 3-(2-{2-[2-(2-aminoethoxy)ethoxy]ethoxy}ethoxy)-4,5-dimethoxybenzaldehyde 14, 4.31 g (12.6 mmol) 2-(1,3-benzodioxol-5-yl)-1-(4-methoxyphenyl)-4-oxobutyric acid methyl ester 3 and 756 mg (14.00 mmol) sodium methoxide were dissolved in 120 ml of methanol at 0° C. and then heated to reflux for 72 hrs under an argon atmosphere. Acetic acid was added (2.0 ml) and the mixture was heated to reflux for further 7 hrs. After evaporation of the solvent the residue was partitioned between water and ethyl acetate. The organic layer was successively washed with water and brine and dried over sodium sulfate. After evaporation of the solvent a yellow oil remains which was purified by silica gel column chromatography (cyclohexane/ ethyl acetate 1/2). Yield: 7.21 g (9.39 mmol, 75%). $^1$H-NMR (CDCl$_3$) δ=7.74 (d, 2H, J=8.8 Hz), 6.96-6.91 (m, 2H), 6.83 (d, 2H, J=8.8 Hz), 6.79 (d, 1H, J=7.5 Hz), 6.15 (s, 1H), 5.99 (s, 1H), 5.96 (s, 2H), 5.67 (br, 1H), 5.11 (br, 1H), 3.96-3.92 (m, 2H), 3.85-3.80 (m, 2H), 3.79 (s, 3H), 3.74 (s, 3H), 3.71-3.68 (m, 2H), 3.67-3.57 (m, 8H), 3.62 (s, 3H), 3.50 (t, 2H, J=5.1 Hz), 3.30-3.22 (m, 2H), 1.41 (s, 9H) ppm. $^{13}$C-NMR δ=171.0, 160.5, 160.1, 156.1, 152.8, 152.0, 148.0, 147.6, 137.0, 131.8, 129.0, 127.9, 127.4, 123.1, 123.0, 113.8, 109.4, 108.3, 107.9, 106.1, 105.8, 101.2, 79.2, 70.6, 70.5, 70.4, 70.1 (2 signals), 69.7, 68.5, 60.7, 60.4, 55.8, 55.3, 32.1, 28.4 ppm. MS: m/z=790 [M+Na]$^+$, 668 [M-(COOtBuH$_2$)]$^+$. HRMS: Calcd. for C$_{40}$H$_{49}$NO$_{14}$Na$^+$ 790.3045, found 790.3032. Anal. calcd for C$_{40}$H$_{49}$NO$_{14}$: C, 62.57, H, 6.43, N, 1.82. Found C, 62.48, H, 6.55, N, 1.80.

3-Benzo[1,3]dioxol-5-yl-3-(2-{2-[2-(2-aminoethoxy) ethoxy]ethoxy}ethoxy)-4,5-dimethoxybenzyl)-5-hydroxy-5-(4-methoxyphenyl)-5H-furan-2-one (TFA salt, 16)

A solution of 4.59 g (5.98 mmol) of the above Boc-protected butenolide 15 in 25 ml methylene chloride was cooled in an ice bath. Trifluoroacetic acid (TFA, 8.0 ml, dissolved in 10.0 ml of methylene chloride) was added dropwise over a period of 30 min. Stirring was continued for 30 min at 0° C. and another 60 min at room temperature. The solvent and excess TFA was removed under vacuum. The remaining viscous oil was treated with methanol and water (10 ml, 2/1) and again evaporated to dryness. An off-white foam remains which does not deliquesce if cooled to 4° C. Yield: 4.66 g (5.97 mmol, 99%). $^1$H-NMR (dmso-d$_6$) δ=8.04 (br, 3H), 7.55 (d, 2H, J=8.8 Hz), 7.12-7.08 (m, 3H), 7.07 (d, 2H, J=8.8 Hz), 6.18 (d, 2H, J=1.5 Hz), 6.15 (s, 1H), 6.13 (s, 1H), 4.00-3.93 (m, 2H), 3.91 (s, 3H), 3.88-3.80 (m, 4H), 3.79-3.74 (m, 6H), 3.73 (s, 3H), 3.70 (s, 3H), 3.64 (s, 4H), 3.15 (q, 2H, J=5.5 Hz) ppm (the proton of the butenolide hydroxy group can not be detected). $^{13}$C-NMR δ=170.7, 161.4, 159.6, 158.3 (q, $J_{C,F}$=−35 Hz), 152.2, 151.3, 147.3, 146.9, 135.9, 131.7, 129.1, 127.6, 126.6, 123.3, 123.0, 116.2 (q, $J_{C,F}$=−295 Hz), 113.6, 109.3, 108.1, 107.2, 106.3, 105.7, 101.2, 69.9, 69.8, 69.7, 69.6, 68.8, 67.8, 66.7, 59.8, 55.4, 55.1, 38.6, 31.4 ppm. $^{19}$F-NMR δ=−74.4 ppm. HRMS: Calcd. for C$_{35}$H$_{42}$NO$_{12}$$^+$ 668.2702, found 668.2707.

Fluorochrome conjugation. The amino-functionalised derivative 16 (1.0 mg, 1.3 μmol) was dissolved in 600 μl of a bicarbonate buffer (0.1 M NaHCO$_3$, pH 8.6). To this was added a solution of Cy 5.5 NHS ester (1.5 mg, 1.3 μmol) in 400 μl DMSO. The solution was vortexed for one hour at room temperature in the dark. Purification of the Cy 5.5-labelled derivative 17 was performed by gradient HPLC using a Knauer system with two K-1800 pumps, an S-2500 UV detector and a RP-HPLC Nucleosil 100-5 C18 column (250 mm×4.6 mm). Eluent A: water (0.1% TFA). Eluent B: Acetonitrile (0.1% TFA). Gradient from 90% A to 40% A over 40 minutes at a flow rate of 1.5 ml/min, detection at λ=254 nm. The appropriate fractions ($t_R$=31 min) were collected, lyophilised, redissolved in PBS and finally stored at −20° C. MS: m/z=521.0 [M]$^{3-}$, 781.9 [M+H]$^{2-}$, 792.8 [M+Na]$^{2-}$, 1564.6 [M+2H]$^-$, 1586.5 [M+H+Na]$^-$, 1608.5 [M+2Na]$^-$ 1630.5 [M−H+3Na]$^-$, 1652.5 [M−2H+4Na]$^-$.

Biology

Tissue preparation. Microsomes were prepared by homogenizing cardiac ventricles from DBA mice at 4° C. for 90 seconds in 1 ml of buffer A (10 mM EDTA, 10 mM HEPES, 0.1 mM benzamidine, pH 7.4), using a Polytron PT 3000 (Kinematica, Lucerne, Switzerland). Homogenates were centrifuged at 45.000× $g_{max}$ for 15 min at 4° C. The pellets were resuspended in 1 ml of buffer B (1 mM EDTA, 10 mM HEPES, 0.1 mM benzamidine, pH 7.4) and recentrifuged at 45.000× $g_{max}$ for 15 min at 4° C. The pellets were resuspended in 1 ml of buffer B and centrifuged at 10.000× $g_{max}$ for 10 min at 4° C. The supernatants were recentrifuged at 45.000× $g_{max}$ for 15 min at 4° C. The pellets, partially enriched ventricular membranes, were resuspended in buffer C (50 mM Tris.HCl, 5 mM MgCl$_2$, pH 7.4) and stored frozen at −80° C.

Competition experiments. For competition binding studies, the prepared membranes were resuspended in buffer D (10 mM Tris-HCl, 154 mM NaCl, 0.1 mM ascorbic acid, pH 7.4) at 0° C. 10 μg of membranes were incubated with a constant concentration of [$^{125}$I]ET-1 (PerkinElmer Live Sciences Inc., Billerica, USA, 40 pM) and with varying concentrations (10 pM-100 μM) of ET antagonist 4 and PD 156707 at 37° C. for 4 hrs. Reactions were stopped by filtering onto Whatman GF/B filters and washed with 0.9% NaCl at 4° C. The membrane bound radioactivity was determined in a γ-scintillation counter. Values for the maximum number of binding sites ($B_{max}$) and the dissociation constant ($K_D$) were determined using the Scatchard method as described in previous papers (30, 39). Competition binding curves were analyzed by nonlinear regression analysis using the XMGRACE programme (Linux software).

Cell binding assays. Cells (HT-1080 fibrosarcomas, MDA-MB435 ductal carcinomas, MCF-7 adenocarcinomas) were seeded in 4-well plates (Nunc GmbH & Co. KG, Wiesbaden, Germany) and incubated in culture medium (0.5 ml/well) overnight. For binding studies cells were washed twice with PBS and resuspended in 150 μl binding buffer (20 mM HEPES in PBS with Ca$^{2+}$/Mg$^{2+}$, 0.2% BSA, 0.1% Glucose, pH 7.4). Cy 5.5 (final amount 5.0 nmol, 33.3 μM) or Cy 5.5 conjugate 17 (5.0 nmol, 33.3 μM) was added into each well. After an incubation period of 45 min at 4° C. cells were washed twice with PBS and were resuspended in binding buffer. For competition assays the parent ET$_A$R antagonist PD 156707 (final amount 50 nmol, 333 μM) or ET$_A$R antibody (1.3 μg) was added to each well for 45 min at 4° C. Cells could be directly visualised by fluorescence microscopy (40× objective, Nikon TE 2000-S, Nikon-Düsseldorf, Germany). The microscope was equipped with a mercury vapour lamp (100 W), 620/775 nm and 545/675 nm (excitation/emission) filters (AHF Analysentechnik, Tübingen, Germany), a Nikon DXM1200F camera and ACT1/DXM1200F software (Nikon, Japan).

Western blot analysis. Confluent (80-100%) HT-1080, MDA-MB-435 and MCF-7 cells were treated with 0.5 ml trypsin and harvested by scraping in cold PBS. After two centrifugation steps (1500 rpm, 5 min, 4° C.) cells were resuspended in lysis buffer (0.5% Tween 20, 50 mM Tris-HCl pH 8, 250 mM NaCl, 5 mM EDTA pH 8, 50 mM NaF, 0.5 mM Na$_3$VO$_4$, 0.9 mg/ml protease inhibitor cocktail, Sigma, St. Louis, USA) and the protein concentration of each sample was determined (Lowry protein assay, total amount 40 μg). To concentrate the protein, a 2-fold volume of cold acetone was added to each sample and placed in −20° C. for 16 hrs, followed by centrifugation at 10.000× $g_{max}$ at 4° C. for 30 min. Protein pellets were dissolved in 100 μl of 6× sodium dodecyl sulfate (SDS) sample buffer (New England Biolabs, Beverley, USA). Following precipitation, proteins were electrophoretically separated in non-reducing 10% SDS-PAGE and transferred to PVDF membranes (Millipore Corporation, Bedford, USA). After blocking, immunoblots were incubated with ET$_A$R polyclonal antibody (N-15, Santa Cruz Biotechnology, Santa Cruz, USA) and with peroxidase-conjugated donkey anti-goat IgG secondary antibody (Sigma, St. Louis, USA). Peroxidase activity was revealed using ECL chemiluminescence (Amersham Biosciences, Freiburg, Germany) and X-ray film, as described by the manufacturers. Human endothelial cell lysate (5 µg, BD Bioscience, San Diego, USA) was used as a positive control.

Chemistry. The synthesis of the butenolide compound 4 was accomplished via the route outlined in scheme 1. Ketoester 3 was synthesised as described by Doherty et. al. by subsequent Aldol condensation, Michael addition and nitrile hydrolysis/esterification (37). Benzaldehyde 2 was accessible by reaction of 3,4-dimethoxy-5-hydroxybenzaldehyde 1 with 1,2-bis(2-chloroethoxy)ethane and caesium carbonate in DMF. We found that the use of caesium carbonate instead of potassium carbonate allows to perform the substitution reactions of these phenolic alcohols with nucleophiles at lower temperature and in shorter reaction times, thereby improving the yield of the desired ethers. Reaction with potassium phthalimide in DMF at elevated temperature gives the product 2 in 61% overall yield. To obtain butenolide 4 kondensation of the benzaidehyde with ketoester 3 was arranged. This is carried out by subsequently adding ketoester 3 and aldehyde 2 to a solution of sodium methylate in methanol at 0° C. and then refluxing the mixture for 12-15 hrs under an inert atmosphere (argon). Finally, the addition of acetic acid and another 5-6 hrs reflux is necessary to obtain the ring-closed butenolide product 4.

The attempt to obtain amino-functionalised products by hydrazinolysis of phthalimidoyl-modified butenolide derivatives like 4 failed. The hydrazine not only reacted with the phthalimidoyl group but also inserted into the butenolide ring, giving a pyridazine derivative (data not shown).

The synthesis of benzaldehyde 8 (schemes 3, 4) started with the preparation of the PEG-spacer. This was achieved in accordance to the procedure described by Tahtaoui et. al. for the corresponding PEG$_3$-derivative and is outlined in scheme 2 (38). Subsequent reaction of triphenylmethanol and methanesulfonyl chloride with tetraethylene glycol yields the trityl-protected, activated PEG derivative 5, which is further converted to the azide 6 by reaction with sodium azide in acetonitrile at reflux. The trityl group is then removed by reaction with p-toluene sulfonic acid in methanol, and the free hydroxy function is again activated with methanesulfonyl chloride, giving 2-{2-[2-(2-azidoethoxy)ethoxy]ethoxy}ethyl methane sulfonate (MsO-PEG$_4$-N$_3$, 7) in 50% overall yield. The coupling of the so modified PEG spacer to 3,4-dimethoxy-5-hydroxybenzaldehyde 1 is again conducted by reaction of the compounds and caesium carbonate in DMF at 80° C. for 4 hrs. The final step includes the reaction of the ketoester 3 with the corresponding aldehyde 8 to yield butenolide 9. This is carried out as described above for benzaldehyde 2 (scheme 1).

Compound 9 is then converted to the free amine 10 by Staudinger-Reaction with triphenylphosphine and water in THF (scheme 3). Regrettably, the yields in this step were disappointing (<20%) and several byproducts made the purification rather difficult. This probably occurred due to reaction of the phosphine with one of the oxygen-containing moieties of the butenolide ring structure. To circumvent these difficulties a second reaction sequence was chosen, where the amine was generated earlier and then protected for further conversion. This second sequence (scheme 4) also starts with the reaction of 3,4-dimethoxy-5-hydroxybenzaldehyde 1 with PEG-derivative 7. The aldehyde function of azide 8 is then protected with ethylene glycol, giving dioxolane 11 in nearly quantitative yield after purification. This kind of protection allows subsequent reduction of the azide and BOC protection of the generated amine 12 without the risk of intermolecular imine formation. The dioxolane protecting group of 13 then can easily be destroyed by reaction with catalytic amounts of iodine in acetone without affecting the BOC protecting group. The product benzaldehyde 14 and ketoester 3 are then converted to the desired butenolide derivative by the same procedure as described above for the azide functionalised aldehyde 8 (scheme 3). The product of this rection is the PEG-modified, N-Boc-protected butenolide 15, which in the finishing step is deprotected by treatment with trifluoroacetic acid (TFA) in methylene chloride. The final product 16 can be isolated as the TFA salt which can be handled and stored easily at 4° C.

Fluorochrome conjugation. The amino functionalised compound 16 was used for the conjugation of cyanine dye Cy 5.5 (used as the corresponding NHS-ester). The reactions were carried out similar to recommended peptide labelling procedures (Amersham Biosciences UK Limited, Buckimhamshire, UK), using an aqueous bicarbonate buffer and DMSO as solvents and reaction conditions of one hour at room temperature. The conjugate 17 was purified by reversed phase HPLC on an analytical column by collection of the appropriate fractions. After lyophilisation and redissolving in PBS the sample showed a purity of >95% (FIG. 1). The identification of the labelled ligand was possible by mass spectrometry with the triply negatively charged ion emerging at 100% intensity.

In vitro competition studies. The affinitiy of the prepared butenolide derivative 4 (scheme 1) towards endothelin receptors was determined by competition binding studies using [$^{125}$I]ET-1 and mouse cardiac ventricular membrane preparations. The binding of [$^{125}$I]ET-1 to ventricular membranes was specific, saturable and of high affinity. Scatchard (39-41) transformation of the saturation data yielded values for the dissociation constant ($K_D$=208±2 pM) and the maximum number of binding sites ($B_{max}$=300±3 fmol/mg protein). The receptor affinity of butenolide 4 is compared to that of the lead compound PD 156707. We found an IC$_{50}$-value of 8.4±1.7 nM for the model compound 4 and a value of 2.2±0.5 nM for the lead compound PD 156707 (37, 0.3 nM, FIG. 2). This encouraging result proves the possibility to modify this small-molecule receptor antagonist with an appropriate spacer group and a larger signalling molecule at the chosen site without affecting its receptor binding potencies.

Western blot analysis. The cellular expression level of the ET$_A$ receptor was determined by western blot analysis (FIG. 3). Using the Santa Cruz polyclonal antibody reveals a low molecular weight band at 38 kDa which corresponds to a proteolytic fragment of the high molecular weight (66 kDa) protein still possessing the ligand binding properties of the receptor (42, 43). The highest amount of protein is found in human fibrosarcoma cells HT-1080, indicated by an intense major band at 38 kDa. A weaker band is found for the human adenocarcinoma cell line MCF-7, indicating a lower amount of ET$_A$ receptor protein while MDA-MB-435 cells do not express ET$_A$ receptors which can be concluded from the absence of the 38 kDa band. Therefore, these cell lines providing different levels of target expression were ideally suited to test the conjugate 17 for receptor targeting efficacy. As a positive control, human endothelial cell lysate was used, also showing an intense band at 38 kDa (FIG. 3).

In vitro cell binding assays. We tested the specific visualisation of the ET$_A$ receptor on positive MCF-7 human breast adenocarcinoma cells, HT-1080 human fibrosarcoma cells and ET$_A$-negative MDA-MB-435 human breast carcinoma cells with the fluorochrome conjugated ligand 17. Binding of the labelled antagonist could be directly analysed by fluorescence microscopy. Negligible signals were detected from the cells when incubated with Cy 5.5 dye alone (5 nmol, data not shown). Incubation of the cells with 2 nmol (33.3 µM) of 17 allowed for visualisation of the $ET_A$ receptor. The signal was distributed over the cell surface and membrane-associated (FIG. 4). Blocking of the signal was possible with 1.3 µg of the $ET_A$ receptor specific antibody (FIG. 4B) or with a tenfold excess of the unlabelled antagonist PD 156707 (data not shown). Interestingly, the $ET_A$ receptor expressing human fibrosarcoma cells HT-1080 showed a higher fluorescence signal than human breast cancer cell line MCF-7 (FIGS. 4A, 4C), while $ET_A$-negative MDA-MB-435 human breast carcinoma cells showed no accumulation of the ligand (FIG. 4D). Thus, these results nicely correlate with the western blot analysis (FIG. 3) and confirm target specific binding of the probe.

The aim of this work was to develop a nonpeptide, highly affine $ET_A$ receptor antagonist which is applicable for optical imaging of $ET_A R$ expression. We chose 3-benzo[1,3]dioxol-5-yl-5-hydroxy-5-(4-methoxyphenyl)-4-(3,4,5-trimethoxy-benzyl)-5H-furan-2-one (PD 156707) as the lead structure and developed a synthetic route towards an amino-PEG-derivatised compound which can be used for the conjugation of common amino-reactive markers. We used Cy 5.5 for conjugation, thus obtaining a near infrared fluorescent photoprobe for the selective imaging of endothelin-A receptors ($ET_A R$). The specificity of binding to $ET_A R$ was shown by western blot analysis and in vitro cell binding assays, respectively. Incubation of human cancer cells with the conjugate lead to the specific visualisation of the $ET_A R$ positive cell lines HT-1080 and MCF-7. The signal was distributed over the cell surface and was membrane-associated. Blocking of the signal was possible with the unlabelled $ET_A R$ antagonist PD 156707 or with an $ET_A R$ specific antibody, verifying specific binding to cell surface sites. The $ET_A R$ negative cell line MDA-MB435 did not show any accumulation of the ligand. The results suggest that the modified photoprobe 17 tightly binds to $ET_A$ receptors, thus representing a potential candidate for the in vivo imaging of $ET_A R$-overexpressing tissues in medical diagnosis.

(1) Hickey, K. A., Rubanyi, G., Paul, R. J., and Highsmith, R. F. (1985) Characterization of a coronary vasoconstrictor produced by cultured endothelial cells. *Am J Physiol* 248, C550-6.

(2) Yanagisawa, M., Kurihara, H., Kimura, S., Tomobe, Y., Kobayashi, M., Mitsui, Y., Yazaki, Y., Goto, K., and Masaki, T. (1988) A novel potent vasoconstrictor peptide produced by vascular endothelial cells. *Nature* 332, 411-5.

(3) Dhaun, N., Goddard, J., and Webb, D. J. (2006) The endothelin system and its antagonism in chronic kidney disease. *J Am Soc Nephrol* 17, 943-55.

(4) Giaid, A., Yanagisawa, M., Langleben, D., Michel, R. P., Levy, R., Shennib, H., Kimura, S., Masaki, T., Duguid, W. P., and Stewart, D. J. (1993) Expression of endothelin-1 in the lungs of patients with pulmonary hypertension. *N Engl J Med* 328, 1732-9.

(5) Pittman, Q. J. (2006) Endothelin—An emerging role in proinflammatory pathways in brain. *Am J Physiol Regul Integr Comp Physiol* 290, R162-3.

(6) Plusczyk, T., Witzel, B., Menger, M. D., and Schilling, M. (2003) ETA and ETB receptor function in pancreatitis-associated microcirculatory failure, inflammation, and parenchymal injury. *Am J Physiol Gastrointest Liver Physiol* 285, G145-53.

(7) Saito, Y., Nakao, K., Mukoyama, M., and Imura, H. (1990) Increased plasma endothelin level in patients with essential hypertension. *N Engl J Med* 322, 205.

(8) Teerlink, J. R., Loffler, B. M., Hess, P., Maire, J. P., Clozel, M., and Clozel, J. P. (1994) Role of endothelin in the maintenance of blood pressure in conscious rats with chronic heart failure. Acute effects of the endothelin receptor antagonist Ro 47-0203 (bosentan). *Circulation* 90, 2510-8.

(9) Grant, K., Loizidou, M., and Taylor, I. (2003) Endothelin-1: A multifunctional molecule in cancer. *Br J Cancer* 88, 163-6.

(10) Levin, E. R. (1995) Endothelins. *N Engl J Med* 333, 356-63.

(11) Nelson, J., Bagnato, A., Battistini, B., and Nisen, P. (2003) The endothelin axis: Emerging role in cancer. *Nat Rev Cancer* 3, 110-6.

(12) Asham, E., Shankar, A., Loizidou, M., Fredericks, S., Miller, K., Boulos, P. B., Burnstock, G., and Taylor, I. (2001) Increased endothelin-1 in colorectal cancer and reduction of tumour growth by ET(A) receptor antagonism. *Br J Cancer* 85, 1759-63.

(13) Bagnato, A., Salani, D., Di Castro, V., Wu-Wong, J. R., Tecce, R., Nicotra, M. R., Venuti, A., and Natali, P. G. (1999) Expression of endothelin 1 and endothelin A receptor in ovarian carcinoma: Evidence for an autocrine role in tumor growth. *Cancer Res* 59, 720-7.

(14) Nelson, J. B., Chan-Tack, K., Hedican, S. P., Magnuson, S. R., Opgenorth, T. J., Bova, G. S., and Simons, J. W. (1996) Endothelin-1 production and decreased endothelin B receptor expression in advanced prostate cancer. *Cancer Res* 56, 663-8.

(15) Alanen, K., Deng, D. X., and Chakrabarti, S. (2000) Augmented expression of endothelin-1, endothelin-3 and the endothelin-B receptor in breast carcinoma. *Histopathology* 36, 161-7.

(16) Wülfing, P., Diallo, R., Kersting, C., Wülfing, C., Poremba, C., Rody, A., Greb, R. R., Boecker, W., and Kiesel, L. (2003) Expression of endothelin-1, endothelin-A, and endothelin-B receptor in human breast cancer and correlation with long-term follow-up. *Clin Cancer Res* 9, 4125-31.

(17) Rosano, L., Varmi, M., Salani, D., Di Castro, V., Spinella, F., Natali, P. G., and Bagnato, A. (2001) Endothelin-1 induces tumor proteinase activation and invasiveness of ovarian carcinoma cells. *Cancer Res* 61, 8340-6.

(18) Salani, D., Di Castro, V., Nicotra, M. R., Rosano, L., Tecce, R., Venuti, A., Natali, P. G., and Bagnato, A. (2000) Role of endothelin-1 in neovascularization of ovarian carcinoma. *Am J Pathol* 157, 1537-47.

(19) Del Bufalo, D., Di Castro, V., Biroccio, A., Varmi, M., Salani, D., Rosano, L., Trisciuoglio, D., Spinella, F., and Bagnato, A. (2002) Endothelin-1 protects ovarian carcinoma cells against paclitaxel-induced apoptosis: Requirement for Akt activation. *Mol Pharmacol* 61, 524-32.

(20) Eberl, L. P., Egidy, G., Pinet, F., and Juillerat-Jeanneret, L. (2000) Endothelin receptor blockade potentiates FasL-induced apoptosis in colon carcinoma cells via the protein kinase C-pathway. *J Cardiovasc Pharmacol* 36, S354-6.

(21) Ali, H., Dashwood, M., Dawas, K., Loizidou, M., Savage, F., and Taylor, I. (2000) Endothelin receptor expression in colorectal cancer. *J Cardiovasc Pharmacol* 36, S69-71.

(22) Bagnato, A., Cirilli, A., Salani, D., Simeone, P., Muller, A., Nicotra, M. R., Natali, P. G., and Venuti, A. (2002) Growth inhibition of cervix carcinoma cells in vivo by endothelin A receptor blockade. *Cancer Res* 62, 6381-4.

(23) Rosano, L., Spinella, F., Salani, D., Di Castro, V., Venuti, A., Nicotra, M. R., Natali, P. G., and Bagnato, A. (2003) Therapeutic targeting of the endothelin A receptor in human ovarian carcinoma. *Cancer Res* 63, 2447-53.

(24) Carducci, M. A., Nelson, J. B., Bowling, M. K., Rogers, T., Eisenberger, M. A., Sinibaldi, V., Donehower, R., Leahy, T. L., Carr, R. A., Isaacson, J. D., Janus, T. J., Andre, A., Hosmane, B. S., and Padley, R. J. (2002) Atrasentan, an

(24) endothelin-receptor antagonist for refractory adenocarcinomas: Safety and pharmacokinetics. *J Clin Oncol* 20, 2171-80.

(25) Carducci, M. A., Padley, R. J., Breul, J., Vogelzang, N. J., Zonnenberg, B. A., Daliani, D. D., Schulman, C. C., Nabulsi, A. A., Humerickhouse, R. A., Weinberg, M. A., Schmitt, J. L., and Nelson, J. B. (2003) Effect of endothelin-A receptor blockade with atrasentan on tumor progression in men with hormone-refractory prostate cancer: A randomized, phase II, placebo-controlled trial. *J Clin Oncol* 21, 679-89.

(26) Yamashita, J., Ogawa, M., Inada, K., Yamashita, S., Matsuo, S., and Takano, S. (1991) A large amount of endothelin-1 is present in human breast cancer tissues. *Res Commun Chem Pathol Pharmacol* 74, 363-9.

(27) Wülfing, P., Götte, M., Sonntag, B., Kersting, C., Schmidt, H., Wülfing, C., Buerger, H., Greb, R., Boecker, W., and Kiesel, L. (2005) Overexpression of Endothelin-A-receptor in breast cancer: Regulation by estradiol and cobalt-chloride induced hypoxia. *Int J Oncol* 26, 951-60.

(28) Wülfing, P., Tio, J., Kersting, C., Sonntag, B., Buerger, H., Wülfing, C., Euler, U., Boecker, W., Tulusan, A. H., and Kiesel, L. (2004) Expression of endothelin-A-receptor predicts unfavourable response to neoadjuvant chemotherapy in locally advanced breast cancer. *Br J Cancer* 91, 434-40.

(29) Davenport, A. P., Kuc, R. E., Fitzgerald, F., Maguire, J. J., Berryman, K., and Doherty, A. M. (1994) [$^{125}$I]-PD151242: A selective radioligand for human ETA receptors. *Br J Pharmacol* 111, 4-6.

(30) Höltke, C., Law, M. P., Wagner, S., Breyholz, H. J., Kopka, K., Bremer, C., Levkau, B., Schober, O., and Schäfers, M. (2006) Synthesis, in vitro pharmacology and biodistribution studies of new PD 156707-derived ET(A) receptor radioligands. *Bioorg Med Chem* 14, 1910-7.

(31) Johnström, P., Aigbirhio, F. I., Clark, J. C., Downey, S. P., Pickard, J. D., and Davenport, A. P. (2000) Syntheses of the first endothelin-A- and -B-selective radioligands for positron emission tomography. *J Cardiovasc Pharmacol* 36, S58-60.

(32) Johnström, P., Fryer, T. D., Richards, H. K., Barret, O., Clark, J. C., Ohistein, E. H., Pickard, J. D., and Davenport, A. P. (2004) In Vivo Imaging of Cardiovascular Endothelin Receptors Using the Novel Radiolabelled Antagonist [$^{18}$F]-SB209670 and Positron Emission Tomography (microPET). *J Cardiovasc Pharmacol* 44, S34-S38.

(33) Mathews, W. B., Zober, T. G., Ravert, H. T., Scheffel, U., Hilton, J., Sleep, D., Dannals, R. F., and Szabo, Z. (2006) Synthesis and in vivo evaluation of a PET radioligand for imaging the endothelin-A receptor. *Nucl Med Biol* 33, 15-9.

(34) Ravert, H. T., Mathews, W. B., Hamill, T. G., Burns, H. D., Dannals, R. F. (2000) Radiosynthesis of a potent endothelin receptor antagonist: [$^{11}$C]-L753037. *J Label Compd. Radiopharm.*, 1205-1210.

(35) Bremer, C., Ntziachristos, V., Weitkamp, B., Theilmeier, G., Heindel, W., and Weissleder, R. (2005) Optical imaging of spontaneous breast tumors using protease sensing 'smart' optical probes. *Invest Radiol* 40, 321-7.

(36) Ntziachristos, V., Bremer, C., Graves, E. E., Ripoll, J., and Weissleder, R. (2002) In vivo tomographic imaging of near-infrared fluorescent probes. *Mol Imaging* 1, 82-8.

(37) Doherty, A. M., Patt, W. C., Edmunds, J. J., Berryman, K. A., Reisdorph, B. R., Plummer, M. S., Shahripour, A., Lee, C., Cheng, X. M., Walker, D. M., and et al. (1995) Discovery of a novel series of orally active non-peptide endothelin-A (ETA) receptor-selective antagonists. *J Med Chem* 38, 1259-63.

(38) Tahtaoui, C., Parrot, I., Klotz, P., Guillier, F., Galzi, J. L., Hibert, M., and Ilien, B. (2004) Fluorescent pirenzepine derivatives as potential bitopic ligands of the human M1 muscarinic receptor. *J Med Chem* 47, 4300-15.

(39) Kopka, K., Wagner, S., Riemann, B., Law, M. P., Puke, C., Luthra, S. K., Pike, V. W., Wichter, T., Schmitz, W., Schober, O., and Schafers, M. (2003) Design of new beta1-selective adrenoceptor ligands as potential radioligands for in vivo imaging. *Bioorg Med Chem* 11, 3513-27.

(40) McGonigle, P., Molinoff, P. B. (1989) Quantitative aspects of drug-receptor interactions., in *Basic Neurochemistry* (Siegel, G., Agranoff, B., Albers, R. W., Molinoff, P. B., Ed.) pp 183-201, Raven Press, New York.

(41) Scatchard, G. (1949) The attractions of proteins for small molecules and ions. *Ann. N.Y. Acad. Sci.*, 660-672.

(42) Hughes, S. J., Wall, N., Scholfield, C. N., McGeown, J. G., Gardiner, T. A., Stitt, A. W., and Curtis, T. M. (2004) Advanced glycation endproduct modified basement membrane attenuates endothelin-1 induced $[Ca^{2+}]_i$ signalling and contraction in retinal microvascular pericytes. *Mol Vis* 10, 996-1004.

(43) Kozuka, M., Ito, T., Hirose, S., Lodhi, K. M., and Hagiwara, H. (1991) Purification and characterization of bovine lung endothelin receptor. *J Biol Chem* 266, 16892-6.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

REFERENCES (WITH THE EXCEPTION OF EXAMPLE 14)

[1] Hickey, K. A.; Rubanyi, G.; Paul, R. J.; Highsmith, R. F. *Am. J. Physiol.* 1985, 248, C550-C556.

[2] Yanagisawa, M.; Kurihara, H.; Kimura, S.; Tomobe, Y.; Kobayashi, M.; Mitsui, Y.; Yazaki, Y.; Goto, K. *Nature* 1988, 332, 411-415.

[3] Saito, Y.; Nakao, K.; Mukoyama, M.; Imura, H. *N. Engl. J. Med.* 1990, 322, 205-211.

[4] Teerlink, J.; Loeffler, B.-M.; Hess, P.; Maire, J.-P.; Clozel, M.; Clozel, J.-P. *Circulation* 1994, 90, 2510-2518.

[5] Giaid, A.; Yanagisawa, M.; Langleben, D.; Michel, R.; Levy, R.; Shennib, H.; Kimura, S.; Masaki, T.; Duguid, W.; Path, F. R. C.; Stewart, D. J. *N. Engl. J. Med.* 1993, 328, 1732-1739.

[6] Doherty, A. M. *J. Med. Chem.* 1992, 35, 1493, 1508.

[7] Masaki, T.; Yanagisawa, M.; Goto, K. *Med. Res. Rev.* 1992, 12, 391-421.

[8] Sakurai, T.; Yanagisawa, M.; Masaki, T. *Trends Pharmacol. Sci.* 1992, 13, 103-108.

[9] Battistini, B.; Chailler, P.; D'Orleans-Juste, P.; Briere, N.; Sirios, P. *Peptides* 1993, 14, 385-389.

[10] Ohistein, F. H.; Arleth, A.; Bryan, H.; Elliott, J. D.; Sung, C. P. Eur. *J. Pharmacol.* 1992, 225, 347-350.

[11] Sakurai, T.; Yanagisawa, M.; Takuwa, Y.; Miyazaki, H.; Kimura, S.; Goto, K.; Masaki, T. *Nature,* 1990, 348, 732-735.

[12] Takayanagi, R.; Kitazumi, K.; Takasaki, C.; Ohnaka, K.; Aimoto, S.; Tasaka, K.; Ohashi, M.; Nawata, H. *FEBS Lett.* 1991, 282, 103-106.

[13] La Douceur, D. M.; Flynn, M. A.; Keiser, J. A.; Reynolds, E.; Haleen, S. J. *Biochem. Biophys. Res. Commun.* 1993, 196, 209-215.

[14] Levin, E. R. *N. Engl. J. Med.* 1995, 333, 356-363

[15] Goldie, R. G. *Clin. Exp. Pharmacol. Physiol.* 1999, 26, 145-148.

[16] Masaki, T. *J. Carsiovasc. Pharmacol.* 2000, 35, S3-S5.

17 Cowburn, P. J.; Cleland, J. G. F. *Eur. Heart J.* 2001, 22, 1772-1784.
18 Barton, M.; Haudenschild, C. C.; d'Uscio, L. V.; Shaw, S.; Munter, K.; Luscher, T. F. *Proc. Natl. Acad. Sci. USA*, 1998, 95(24), 14367-14372.
19 Kobayashi, T.; Miyauichi, T.; Iwasa, S.; Sakai, S.; Fan, J.; Nagata, M.; Goto, K.; Watanabe, T. *Pathol. Int.* 2000, 50, 929-936.
20 Davenport, A. P.; Battistini, B. *Clinical Science*, 2002, 103 (Suppl. 48), S1-S3.
21 Webb, M. L.; Meek, T. D. *Med. Res. Rev.* 1997, 17, 17-67.
22 Cheng, X. M.; Doherty, A. M. *Curr. Med. Chem.* 1994, 1, 271-312.
23 Cheng, X. M.; Ahn, K.; Haleen, S. J. *Ann. Rep. Med. Chem.* 1997, 32, 61-70.
24 Boyd, S. A.; Mantei, R. A.; Tasker, A. S.; Liu, G.; Sorensen, B. K.; Henry, K. J. Jr.; von Geldern, T. W.; Winn, M.; Wu-Wong, J. R.; Chiou, W. J.; Dixon, D. B.; Hutchins, C. W.; Marsh, K. C.; Nguyen, B.; Opgenorth, T. *J. Bioorg. Med. Chem.* 1999, 7, 991-1002.
25 Neidhart, W.; Breu, V.; Burri, K.; Clozel, M.; Hirth, G.; Klinkhammer, U.; Giller, T.; Ramuz, H. *Bioorg. Med. Chem. Lett.* 1997, 7, 2223-2228.
26 Sakaki, J.; Murata, T.; Yuumoto, Y.: Nakamura, I.; Frueh, T.; Pitterna, T.; Iwasaki, G.; Oda, K.; Yamamura, T.; Hayakawa, K. *Bioorg. Med. Chem. Lett.* 1998, 8, 2241-2246.
27 Amberg, W.; Hergenröder, S.; Hillen, H.; Jansen, R.; Kettschau, G.; Kling, A.; Klinge, D.; Raschak, M.; Riechers, H.; Unger, L. *J. Med. Chem.* 1999, 42, 3026-3032.
28 Kopetz, S.; Nelson, J. B.; Carducci, M. A. *Inv New Drugs* 2002, 20, 173-182.
29 Nelson, J. B.; Bagnato, A.; Battistini, B.; Nisen, P. *Nature Rev. Cancer*, 2003, 3, 110-116.
30 Wu-Wong, J. R.; Chiou, W. J.; Dickinson, R.; Opgenorth, T. J. *Biochem. J.* 1997, 328, 733-737.
31 Fowler, J. S.; Volkow, N. D.; Wang, G.-J.; Ding, Y.-S.; Dewey, S. L. *J. Nucl. Med.* 1999, 40, 1154-1163.
32 Phelps, M. E. *J. Nucl. Med.* 2000, 41, 661-681.
33 Neglia, D.; Sambuceti, G.; Iozzo, P.; L'Abbate, A.; Strauss, W. H. Eur. *J. Nucl. Med. Mol. Imag.* 2002, 29, 1403-1413.
34 Davenport, A. P.; Kuc, R. E.; Fitzgerald, F.; Maguire, J. J.; Berryman, K.; Doherty, A. M. *Br. J. Pharmacol.* 1994, 111, 4-6.
35 Davenport, A. P.; Kuc, R. E.; Ashby, M. J.; Patt, W. C.; Doherty, A. M. *Br. J. Pharmacol.* 1998, 123, 223-230.
36 Ihara, M.; Saeki, T.; Fukuroda, T.; Kimura, M. S.; Ozaki, S.; Patel, A. C.; Yano, M. A. *Life Sci.* 1992, 51, 47-52.
37 Molenaar, P.; Kuc, R. E.; Davenport, A. P. *Br. J. Pharmacol.* 1992, 107, 637-639.
38 Watakabe, T.; Urade, Y.; Takai, M.; Umemura, I.; Okada, T. *Biochem. Biophys. Res. Commun.* 1992, 185, 867-873.
39 Johnstroem, P.; Aigbirhio, F. I.; Clark, J. C.; Downey, S. P. M. J.; Pickard, J. D.; Davenport, A. P. *J. Cardiovasc. Pharmacol.* 2000, 36, S58-S60.
40 Johnstroem, P.; Harris, N. G.; Fryer, T. D.; Barret, O.; Clark, J. C.; Pickard, J. D.; Davenport, A. P. *Clin. Sci.* 2002, 103 (Suppl. 48), S4-S8.
41 Ravert, H. T.; Mathews, W. B.; Hamill, T. G.; Burns, H. D.; Dannals, R. F. *J. Labelled Cmp. Radiopharm.* 2000, 43, 1205-1210.
42 Aleksic, S.; Szabo, Z.; Scheffel, U.; Ravert, H. T.; Mathews, W. B.; Kerenyi, L.; Rauseo, P. A.; Gibson, R. E.; Burns, H. D.; Dannals, R. F. *J. Nucl. Med.* 2001, 42, 1274-1280.
43 Reynolds, E. E.; Keiser, J. A.; Haleen, S. J.; Walker, D. M.; Davis, L. S.; Olszewski, B.; Taylor, D. G.; Hwang, O.; Welch, K. M.; Flynn, M. A.; Thompson, D. M.; Edmunds, J. J.; Berryman, K. A.; Lee, C.; Reisdorph, B. R.; Cheng, X.-M.; Doherty, A. M.; Patt, W. C. *J. Pharmacol. Exp. Ther.* 1994, 273, 1410-1417.
44 Doherty, A. M.; Patt, W. C.; Edmunds, J. J.; Berryman, K. A.; Reisdorph, B. R.; Plummer, M. S.; Shahripour, A.; Lee, C.; Cheng, X.-M.; Walker, D. M.; Haleen, S. J.; Keiser, J. A.; Flynn, M. A.; Welch, K. M.; Hallak, H.; Taylor, D. G.; Reynolds, E. E. *J. Med. Chem.* 1995, 38, 1259-1263.
45 Patt, W. C.; Edmunds, J. J.; Repine, J. T.; Berryman, K. A.; Reisdorph, B. R.; Lee, C.; Plummer, M. S.; Shahripour, A.; Haleen, S. J.; Keiser, J. A.; Flynn, M. A.; Welch, K. M.; Reynolds, E. E.; Rubin, E. E.; Tobias, B.; Hallak, H.; Doherty, A. M. *J. Med. Chem.* 1997, 40, 1063-1074.
46 Scatchard, G. *Ann. N.Y. Acad. Sci.* 1949, 51, 660-672.
47 McGonigle, P.; Molinoff, P. B. In *Basic Neurochemistry*, Siegel, G.; Agranoff, B.; Albers, R. W.; Molinoff, P. B., Editors.; Raven Press: New York, 1989; 4. Ed, pp. 183-201.
48 Cheng, Y.; Prusoff, W. H. *Biochem. Pharmacol.* 1973, 22, 3099-3108.
49 Patt, W. C.; Cheng, X.-M.; Repine, J. T.; Lee, C.; Reisdorph, B. R.; Massa, M. A.; Doherty, A. M.; Welch, K. M.; Bryant, J. W.; Flynn, M. A.; Walker, D. M.; Schroeder, R. L.; Haleen, S. J.; Keiser, J. A. *J. Med. Chem.* 1999, 42, 2162-2168.
50 Astles, P. C.; Brown, T. J.; Halley, F.; Handscombe, C. M.; Harris, N. V.; Majid, T. N.; McCarthy, C.; McLay, I. M.; Morley, A.; Porter, B.; Roach, A. G.; Sargent, C.; Smith, C.; Walsh, R. J. A. *J. Med. Chem.* 2000, 43, 900-910.
51 Jae, H.-S.; Winn, M.; von Geldern, T. W.; Sorensen, B. K.; Chiou, W. J.; Nguyen, B.; Marsh, K. C.; Opgenorth, T. J. *J. Med. Chem.* 2001, 44, 3978-3984.

The invention claimed is:

1. An endothelin receptor antagonist conjugate of formula (I)

wherein $R_2$ is an alkoxy group and one of $R_1$ and $R_3$ represents an alkoxy group and the other represents a group of the formula: $(OCH_2CH_2)_n$—NH—X, wherein n is an integer ranging from 1 to 100 and X is a fluorescent dye or a tautomer thereof.

2. The compound of claim 1 wherein $R_1$ and $R_2$ are —$OCH_3$.

3. The compound of claim 1, wherein n is 4.

4. The compound of claim 1, wherein the fluorescent dye possesses an absorption maximum from about 600 nm to 850 nm.

5. The compound of claim 1, wherein the fluorescent dye is selected from Cy 5, Cy 5.5, Cy 7, C 3, Cy 3.5, fluorescein (FITC), heptamethylene thiocyanine, ROX, TAMRA, CAL Red, Red 640, FAM, TET, HEX, Oregon Green, TRITC, APC, DY-751, ATTO 740, ATTO 725 and ATTO 700.

6. The compound of claim 1, selected from
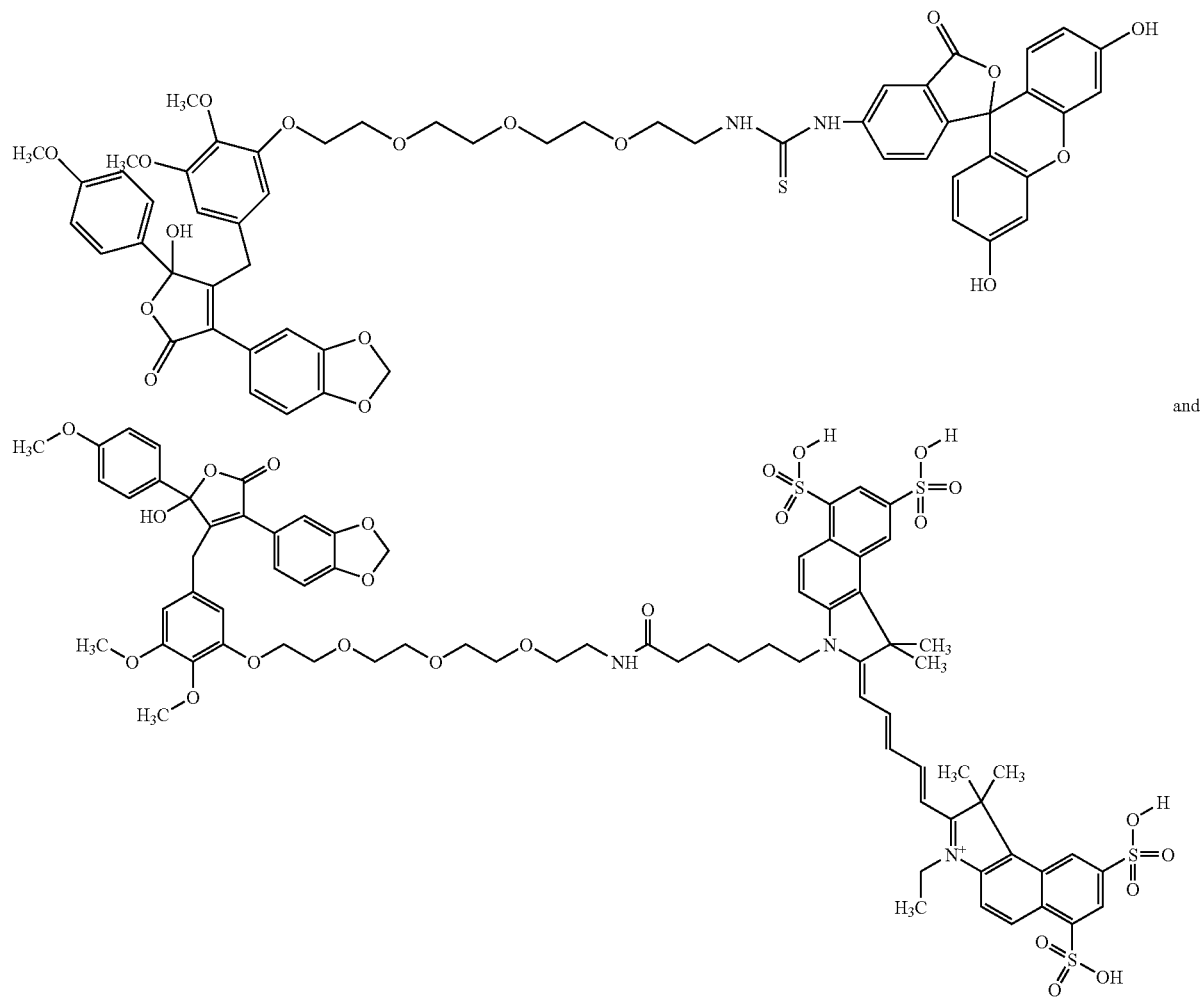
and tautomers thereof.
7. A diagnostic composition comprising the compound of claim 1 and, optionally, a diagnostic carrier.